United States Patent
Polo et al.

(10) Patent No.: US 6,767,699 B2
(45) Date of Patent: Jul. 27, 2004

(54) METHOD FOR THE QUANTITATION OF ALPHAVIRUS REPLICON PARTICLES

(75) Inventors: John M. Polo, Hayward, CA (US); Catherine Greer, Oakland, CA (US); Thomas W. Dubensky, Jr., Piedmont, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/872,086

(22) Filed: May 31, 2001

(65) Prior Publication Data

US 2002/0015945 A1 Feb. 7, 2002

Related U.S. Application Data

(60) Provisional application No. 60/208,376, filed on May 31, 2000.

(51) Int. Cl.[7] .............................. C12Q 1/70; C12Q 1/00; C12N 15/00
(52) U.S. Cl. ............................. 435/5; 435/4; 435/320.1; 435/34; 435/173.9; 424/218.1
(58) Field of Search ............................. 435/320.1, 4, 5, 435/34, 173.9; 424/218.1

(56) References Cited

U.S. PATENT DOCUMENTS

| | | | |
|---|---|---|---|
| 5,026,686 A | 6/1991 | Schlesinger et al. | |
| 5,091,309 A | 2/1992 | Schlesinger et al. | |
| 5,185,440 A | 2/1993 | Davis et al. | |
| 5,217,879 A | 6/1993 | Huang et al. | |
| 5,505,947 A | 4/1996 | Johnston et al. | |
| 5,532,154 A | 7/1996 | Brown | |
| 5,591,579 A | 1/1997 | Olivo et al. | |
| 5,614,404 A | 3/1997 | Mazzara et al. | |
| 5,643,576 A | 7/1997 | Johnston et al. | |
| 5,691,177 A | 11/1997 | Guber et al. | |
| 5,739,026 A | 4/1998 | Garoff et al. | |
| 5,766,602 A | 6/1998 | Xiong et al. | |
| 5,789,245 A | * 8/1998 | Dubensky, Jr. et al. | .. 435/320.1 |
| 5,792,462 A | 8/1998 | Johnston et al. | |
| 5,797,870 A | 8/1998 | March et al. | |
| 5,811,407 A | 9/1998 | Johnston et al. | |
| 5,814,482 A | 9/1998 | Dubensky, Jr. et al. | |
| 5,837,503 A | 11/1998 | Doglio et al. | |
| 5,843,712 A | 12/1998 | Levine | |
| 5,843,723 A | 12/1998 | Dubensky, Jr. et al. | |
| 5,851,757 A | 12/1998 | Olivo et al. | |
| 6,015,686 A | 1/2000 | Dubensky, Jr. et al. | |

FOREIGN PATENT DOCUMENTS

| | | |
|---|---|---|
| EP | 0 198 386 A2 | 10/1986 |
| EP | 0 647 716 A1 | 4/1995 |
| WO | WO 88/00472 | 1/1988 |
| WO | WO 89/10973 | 11/1989 |
| WO | WO 91/02805 | 3/1991 |
| WO | WO 92/06693 | 4/1992 |
| WO | WO 92/10578 | 6/1992 |
| WO | WO 93/25670 | 12/1993 |
| WO | WO 94/17813 | 8/1994 |
| WO | WO 94/26912 | 11/1994 |
| WO | WO 95/07994 | 3/1995 |
| WO | WO 95/17525 | 6/1995 |
| WO | WO 95/19990 | 7/1995 |
| WO | WO 95/25788 | 9/1995 |
| WO | WO 95/27044 | 10/1995 |
| WO | WO 95/27069 | 10/1995 |
| WO | WO 95/31565 | 11/1995 |
| WO | WO 95/32733 | 12/1995 |
| WO | WO 96/17072 | 6/1996 |
| WO | WO 96/37616 | 11/1996 |
| WO | WO 96/39830 | 12/1996 |
| WO | WO 97/08298 | 3/1997 |
| WO | WO 97/16169 | 5/1997 |
| WO | WO 97/24447 | 7/1997 |
| WO | WO 97/30155 | 8/1997 |
| WO | WO 97/38087 | 10/1997 |
| WO | WO 97/44446 | 11/1997 |
| WO | WO 98/13511 | 4/1998 |
| WO | WO 98/15636 | 4/1998 |
| WO | WO 98/53077 | 5/1998 |
| WO | WO 98/26084 | 6/1998 |
| WO | WO 98/36779 | 8/1998 |
| WO | WO 99/09192 | 2/1999 |
| WO | WO 99/11808 | 3/1999 |
| WO | WO 99/15641 | 4/1999 |
| WO | WO 99/18226 | 4/1999 |
| WO | WO 99/25858 | 5/1999 |
| WO | WO 99/25859 | 5/1999 |
| WO | WO 99/30734 | 6/1999 |

OTHER PUBLICATIONS

Acsadi et al., "Human Dystrophin Expresison in mdx Mice After Intramuscular Injection DNA Constructs," *Nature* 352:815–818 (Aug. 1991).

Altman et al., "Contransfection of ICAM–1 and HLA–DR Reconstitutes Human Antigen–Presenting Cell Function in Mouse L Cells," *Nature* 338:512–514 (1989).

Anderson et al., "Alternate Splicing of mRNAs Encoding Human Mast Cell Growth Factor and Localization of the Gene to Chromosome 12q22–q24," *Cell Growth and Differentiation* 2:373–378 (1991).

Autiero et al., "Binding CD4 of Synthetic Peptides Peptides Patterned on the Principal Neutralizing Domain of the HIV–1 Envelope Protein," *Virology* 185:820–828 (1991).

(List continued on next page.)

*Primary Examiner*—James Housel
*Assistant Examiner*—Stacy B. Chen
(74) *Attorney, Agent, or Firm*—Dahna S. Pasternak; Michael J. Moran; Robert P. Blackburn

(57) ABSTRACT

Methods of production and purification for viruses and virus-derived vectors, including those related to alphaviruses, are disclosed. In one aspect, methods of purification that subject alphavirus replicon particle preparations to one or more steps of chromatographic purification, such as using an ion exchange resin, are provided. Also disclosed are methods of characterizing alphavirus replicon particles and utilizing these materials for vaccines and gene-based therapeutics.

5 Claims, 12 Drawing Sheets

OTHER PUBLICATIONS

Ballay et al., "In vitro and in vivo Synthesis of Synthesis of the Hepatitis B Virus Surface Antigen and of the Receptor for Polymerized Human Serum Albumin From Recombinant Human Adenovirus," *EMBO Journal* 4:3861–3865 (1985).

Barbieri et al., "Purification and Partial Characterization of Another Form of the Antiviral Protein from the Seeds of *Phyrolacca americana* L. (pokeweed)," *Biochem. J.* 203:55–59 (1982).

Barneveld et al., "Monoclonal Antibodies Against Human Beta–Glucocerebrosidase," *Eur. J. Biochem.* 134:585–589 (1989).

Barranger et al, The Metabolic Basis of Inherited . . . , vol. 2, $6^{th}$ Ed., Chapter 67, "Glucosylceramide Lipidoses: Gaucher Disease" pp 1677–1698 (1990).

Baumann and Schendel, "Interleukin–11 Regulates the Hepatic Expression of the Same Plasma Protein Genes as Interleukin–6," *Journal of Biological Chemistry* 266:20424–20427 (1991).

Beier et al., "Association of Human Class I MHC Alleles With the Adenovirus E3/19K Protein," *J. Immunology* 152:3862–3872 (1994).

Berglund et al., "Semliki Forest Virus Expression System: Production of Conditionally Infectious Recombinant Particles," *Biotechnology* (N.Y) 11(8):916–920 (1993).

Berglund et al., Alphaviruses as Vectors for Gene Delivery, *Trends Biotechnol.* 14(4):130–134 (1996).

Beauchemin et al., "Isolation and Chacterization of Full-Length Functional cDNA Clones for Human Carcinoembryonic Antigen," *Molecular and Cellular Biology* 7(9):3221–3230 (1987).

Beutler, "Gauche Disease: New Molecular Approaches to Diagnosis and Treatment," *Science* 256:794–799 (1992).

Boyer and Haenni, "Infectious Transcripts and cDNA Clones of RNA Viruses," *Virology* 198:415–426 (1994).

Bredenbeek et al., "Animal RNA Virus Expression Systems," *Seminars in Virology* 3:297–310 (1992).

Bredenbeek et al., "Sindbis Virus Expression Vectors: Packaging of RNA Replicons by Using Defective Helper RNAs," *J. Virol.* 67(11):6439–6446 (1993).

Browne et al., "A Complex Between the MH C Class I Homologue Encoded by Human Cytomegalovirus and Beta 2 Microglobulin," *Nature* 347:770–772 (1990).

Bzik et al., "Molecular Cloning and Sequence Analysis of the Plasmodium Falciparum Dihydrofolate Reductase–Thymidylate Synthase Gene," *Proc. Natl. Acad. Sci. U.S.A.* 84:8360–8364 (Dec. 1987).

Calderwood et al., "Nucleotide Sequence of the Shiga–Like Toxin Genes of *Escherichia coli*," *Proc. Natl. Acad. Sci. U.S.A.* 84:4364–4368 (1987).

Caroll et al., "Active–Site of Pseudomonas *Aeruginosa* exotoxin A," *J. Biological Chemistry* 262(18):8707–8711 (1987).

Chen et al., "The Complete Primary Structure of Abrin–a–B Chain," *Fed. Eur. Biochemical Societies* 309:115–118 (1992).

Chin et al., "Tissue–Specific Expression of Hepatic Function," *Ann. NY Acad. Sci.* 478:120–130 (1986).

Choi et al., "Expression of Human Immunodefici(15):8665–8669 (1990)ency Virus Type 1 (HIV–1) gag, pol, and env. Proteins from Chimeric HIV–1–Polovirus Minireplicons," *J. Virology* 65(6):2875–2883 (1991).

Collins et al., "Primary Amino Acid Sequence of □–Trichosanthin and Molecular Models for Abrin A–cahin and □–trichosanthin," *J. Biological Chemistry* 265(15):8665–8669 (1990).

Correll et al., "High Levels of Human Glucocerebrosidase Activity in Macrophases of Long–Term Reconstituted Mice After Retroviral Infection of Hematopoietic Stem Cells," *Blood* 80(2):331–336 (1992).

Coussens et al., "Tyrosine Kinase receptor with Extensive Homology of EGF Receptor Shares Chromosomal Location with new Oncogene," *Science* 230:1132–1139 (1985).

Culver and Blaese," Gene Therapy for Cancer," *TIG* 10(5):174–178 (1994).

Davis et al., "In Vitro Synthesis of Infectious Venezuelan Equine Encephalitis Virus RNA rom a cDNA Clone: Analysis of a Viable Deletion Mutant," *Virology* 171(1):189–204 (1989).

Davis et al., Protection Against Influenza in Mice By Vaccination With a Venezuelan Equine Encephalitis Virus Vector Expressing the HA Protein, *J. Cell. Biochm. Suppl.* 19A:310, Abstract No. J2–308, (1995).

Driver et al. "Layered Amplification of Gene Expression with a DNA Gene Delivery System," *Annals of New York Academy of Sciences* 772(1):261–264 (1995).

Dryga et al., "Identification of Mutations in a Sindbis Virus Variant Able to Establish Persistent Infection in BHK Cells: The Importance of a Mutation in the nsP2 Gene," *Virology* 228 74–83 (1997).

Dubensky et al., "Sindbis Virus DNA–Based Expression Vectors: Utility for In Vitro and In Vivo Gene Transfer," *Journal of Virology* 70(1):508–519 (1996).

Dubensky et al., "Direct Transfection of Viral and Plasmid DNA Into the Liver or Spleen of Mice," *Proc. Natl. Acad. Sci. U.S.A.* 81:7529–7533 (Dec. 1984).

Dubensky et al., "Polynucleotide Based Gene Transfer Vector Derived From an Alphavirus," *Journal of Cellular Biochemistry Supplement* 0(21A): p. 406, Abstract No. C6–413 (1995).

Dubuisson and Ricje, "Sindbis Virus Attachment: Isolation and Characterization of Mutants with Impaired Binding to Bertebrate Cells," *J. Virology* 67(6):3363–3374 (1993).

Evans et al., "An Enginered Poliovirus Chimera Elicits Broadly Reactive HIV–1 Neutralizing Antibodies," *Nature* 339:385–388 (1989).

Evensen et al., "Direct Molecular Cloning and Expression of Two Distinct Abrin A–Chain," *J. Biological Chemistry* 266(1):6848–6852 (1991).

Fainstein et al., "Nucleotide Sequence Analysis of Human abl and bcr–abl cDNAs," *Oncogene* 4:1477–1481 (1989).

Field et al., "Isolation and Characterization of AcyclovirResistant Mutants of Herpes Simplex Virus," *J. Gen. Virol.* 49:115–124 (1980).

Fisher–Hoch et al., "Protection of rhesus Monkeys from Fatal Lassa Fever by Vaccination with a Recombinant Vaccinia Virus Containing the Lass Virus Glycoprotein Gene," *Proc. Natl. Acad. Sci. U.S.A.*86:317–321 (1989).

Flexner et al., "Attenuation and Immunogenicity in Primates of Vaccinia Virus Recombinants Expressing Human Interleukin–2," *Vaccine* 8:17–21 (1990).

Fox, "No Winners Against AIDS," *Bio/Technology* 12:pp128 (1994).

Frolov and Schlesinger, "Comparison of the Effects Sindbis Virus and Sindbis Virus Replicons on Host Cell Protein Synthesis and Cytopathogenicity in BHK Cells," *J. Virol.* 68(3):1721–1727 (1994).

Frolov et al., "Sindbis Virus Replicons and Sindbis Virus: Assembly of Chimeras and of Particles Deficient in Virus RNA," *J. Virol.* 71(4):2819–2829 (Apr. 1997).

Frolov et al., "Alphavirus–Based Expression Vectors: Strategies and Applications," *Proc. Natl. Acad. Sci. U.S.A.* 93:11371–11377 (Oct. 1996).

Gassman et al., "Analysis of the *Borrelia burgdorferi GeHo fla* Gene and Antigenic Characterization of its Gene Product," *J. Bacteriology* 173(4):1452–1459 (1991).

Geigenmüller–Gnirke et al, "Complementation Between Sindbis Viral RNAs Produces Infectious Particles with a Biparti Genome," *Proc. Natl. Acad. Sci. U.S.A.* 88:3253–3257 (1991).

Grakoui et al., "A cis–Acting Mutation in the Sindbis Virus Junction Region Which Affects Subgenomic RNA Synthesis," *Journal of Virology* 63(12):5216–5227 (1989).

Hahn et al., "Infectious Sindbis Virus Transient expression Vectors for Studying Antigen Processing and Presentation," *Proc. Natl. Acad. Sci. U.S.A.* 89:2679–2683 (Apr. 1992).

Hampel et al., "Hairpin Catalytic RNA Model: Evidence for Helices and Sequences Requirement for Substrate RNA," *Nucleic Acids Research* 18(2):299–304 (1990).

Hariharan et al., "DNA Immunization against Herpes Simplex Virus: Enhanced Efficacy Using a Sindbis Virus–Based Vector," *Journal of Virology* 72:950–958 (1998).

Haseloff et al, "Simple RNA Enzymes with New and Highly Specific Endoribonuclease Activities," *Nature* 334:585–591 (Aug. 1988).

Hertz and Huang, "Utilization of Heterologous Alphavirus Junction Sequences as Promoters by Sindbis Virus," *Journal of Virology* 66(2):857–864 (1992).

Herweijer et al., "A Plasmic–Based Self–Amplifying Sindbis–Based Self–Amplifying Sindbis Virus Vector," *Human Gene Therapy* 6:1161–1167 (1995).

Hevey et al., "Marburg Virus Vaccines Based Upon Alphavirus Replicons Protected Guinea Pigs and Nonhuman Primates," *Virology* 251(1):28–37 (1998).

Hodgson, "Advances in Vectory Systems for Gene Therapy," *Exp. Opin. Ther. Patents* 5(5):459–468 (1995).

Huang et al., "RNA Viruses as Gene Expression Vectors," *Vinus Genes* 3(1):85–91 (1989).

Huang et al., "Liposomal Gene Delivery: A Complex Package," *Nat. Biotechnol.* 15(7):620–621 (1997).

Irvin et al., "Purification and Properties of a Second Antiviral Protein from *Phytolacca americana* which Inactivates Eukaryotic Ribosomes," *Archives of Biochemistry and Biophysics* 200(2):418–425 (1980).

Irvin et al., "Purification and Partial Characterization of the Antiviral Protein from *Phytolacca americana* which Inhibits eukaryotic Protein Synthesis," *Archives of Biochemistry and Biophysics* 169:522–528 (1975).

Jackson et al., "Nucleotide Sequence Analysis of the Structural Genes for Shiga–Like Toxin I Encoded by Bacteriophage 900J from *Escherichia coli*," *Microbial. Pathogenesis* 2:147–153 (1987).

Jang et al., "Initiation of Protein Synthesis by Internal Entry of Ribosomes into the Montranslated Region of Encephalomycarditis Virus RNA in vivo," *J. Virology* 63(4):1651–1660 (Apr. 1989).

Johanning et al., "A Sindbis Virus mRNA Polynucleotide Vector Achieves Prolonged and High Level Heterologous Gene Expression in vivo," *Nucleic Acids Research* 23(9):1495–1501 (1995).

Jolly, "Viral Vector Systems for Gene Therapy," *Cancer Gene Therapy* 1(1):51–64 (1994).

Kekule et al., "The preS2/S Region of Integrated Hepatitis B Virus DNA Encodes a Transcriptional Transactivator," *Nature* 343:457–461 (1990).

Kuhn et al, "Infectious RNA Transcripts form Ross River Virus cDNA Clones and the Construction and Characterization of Defined Chimeras with Sindbis Virus," *Virology* 182:430–441 (1991).

Kuo et al., "An Assay for Circulating Antibodies to a Major Etiologic Virus of Human Non–A, Non–B Hepatitis," *Science* 244:362–364 (1989).

Lamb et al., "Nucleotide Sequence of Cloned cDNA for Preproricin," *Eur. J. Biochem.* 148:265–270 (1985).

Landis et al., "Human MxA Protein Confers Resistance to Semliki Forest Virus and Inhibits the Amplification of a Semliki Forest Virus–Based Replicon in the Absence of Viral Structural Proteins," *J. Virol.* 72(2):1516–1522 (1998).

Lastarza et al., "Deletion and Duplication Mutations in the C–Terminal Nonconserved Region of Sindbis Virus NsP3:Effects on Phosphorylation and on Virus Replication and Invertebrate Cells," *Virology* 202:224–232 (1994).

Lemm et al., "Mutations Which Alter the Level or Structure of nsP4 can Affect the Efficiency of Sindbis Virus Replicatin in a Host–Dependent Manner," *J. Virology* 64(6):3001–3011 (1990).

Lemm et al., "Polypeptide Requirements for Assembly of Functional Sindbis Virus Replication Complexes: a Model for Temporal Regulation of Minus–and Plus–Strand RNA Syntesis," *The EMBO J.* 13(12):2925–2934 (1994).

Letvin, "Progress in the Development of an HIV–1 Vaccine," *Science* 280:1875–1880 (1998).

Levine et al., "Conversion of Lytic to Persistent Alphavirus Infection by the bci–2 Cellular Oncogene," *Nature* 361:739–742 (1993).

Levis et al., "Promoter for Sindbis Virus RNA–Dependent Subgenomic RNA Transcription," *Journal of Virology* 64(4):1726–1733 (1990).

Levis et al., "Deletion Mapping of Sindbis Virus DI RNAs Derived from cDNAs Defines the Sequences Essential for Replication and Packaging," *Cell* 44:137–145 (1986).

Levis et al., "Engineered Defective Interfering RNAs of Sindbis Virus Express Bacterial Chloramphenicol Acetyltransferase in Avian Cells," *Proc. Natl. Acad. Sci. U.S.A.* 84:4811–4815 (1987).

Lijestrom et al., "A New Generation of Animal Cell Expression Vectors Based on the Semliki Forest Virus Replicon," *Biotechnology* (NY) 9(12):1356–1361 (1991).

Lijestrom, P., "Alphavirus Expression Systems," *Currl Opin. Biotechnol.* 5(5):495–500 (1994).

London et al., "Infection Enveloped RNA, Virus Antigenic Chimeras," *Proc. Natl. Acad. Sci. U.S.A.* 89:207–211 (Jan. 1992).

Luo et al., "Purification and Characterization of Sindbis Virus–Induced Peptide Which Stimulates its own Production and Blocks Virus RNA Synthesis," *Virology* 194(1):44–49 (1993).

Maher et al., "Specific Hybridization Arrest of Dihydrofolate Reductase mRNA in vitro Using Anti–Sense RNA of Anti–Sense Oligonucleotides," *Archives of Biochemistry and Biophysics* 253(1):214–220 (1987).

Mansour et al., "An Adenovirus Bector System Used to Express Polyoma Virus tumor Antigens," *Proc. Natl. Acad. Sci. U.S.A.* 82:1359–1363 ( Mar. 1985).

Marshall, "Gene Therapy's Growing Pains," *Science* 269:1050–1055 (1995).

McKnight, "The Nucleotide Sequence and Transcript map of the Herpes Simplex Virus Thymidine Kinase Gene," *Nucleic Acids Research* 8(24):5949–5964 (1980).

Mekalanos et al., "Cholera Toxin Genes: Nucleotide Sequence, Deletion Analysis and Vaccine Development," *Nature* 306:551–557 (Dec. 1983).

Miller and Vile, "Targeted Vectors for Gene Therapy," *FASEB J.* 9:190–199 (1995).

Nolta et al., "Retroviral Vector–Mediated Gene Transfer into Primitive Human Hemotopoietic Progenitor Cells: Effects of Mast Cell Growth Factor (MGF combined with Other Cytokines," *Exp. Hematol.* 20:1065–1071 (1992).

Ohashi et al., "Efficient Transfer and Sustained High Expression of the Human Glucocerebrosidase Gene in Mice and Their Functional Macrophages Following Transplantation of Bone Marrow Transduced by a Retroviral Vector," *Proc. Natl. Acad. Sci. U.S.A.*89:11332–11336 (1992).

Oker–Blom and Summers, "Expression of Sindbis Virus 26S cDNA in Spodoptera Frugiperda (Sf9) Cells. Using a Baculovirus Expression Vector," *Journal of Virology* 63(3):1256–1264 (1989).

Olivo et al., "A Cell Line that Expresses a Reporter Gene in Response to Infection by Sindbis Virus: A Prototype for Detection of Positive Strand RNA Viruses," *Virology* 198:381–384 (1994).

Orkin et al., Report and Recommendations of the Panel to Assess the NIH Investment in Research on Gene Therapy. On the Internet www.nih.gon/news/paneltrep.html. (1995).

Owen and Kuhn, "Identification of a Region in the Sindbis Virus Nucleocapsid Protein That is Involved in Specificity of RNA Encapsidation," *Journal of Virology* 70(5):2757–2763 (1996).

Peters and Dalrymple, Chapter 26, entitled "Alphaviruses," *Virology* second edition, edited b y B.N. Fields, D.M. Knipe et al., Raven Press, Ltd., New York, (1990).

Polo et al., "Alphavirus Mediated Delivery of Ribozyme Therapeutics," *J. Cell Biochem. Suppl. 19A*:228 abstract No. A6–413 (1995).

Polo et al., "Stable Alphavirus Packaging Cell Lines for Sindbis Virus and Semliki Forest Virus–Derived Vectors," *Proc. Natl. Acad. Sci. U.S.A.* 96(8):4598–4603 (Apr. 1999).

Pushko et al., "Replicon–Helper Systems for Attenuated Venezuelan Equine Encephalitis Virus: Expression of Heterologous Genes in vitro and Immunization Against Heterologous Pathogens in vivo," *Virology* 239(2):389–401 (1997).

Racaniello and Baltimore, "Cloned Poliovirus Complementary DNA is Infectious in Mammalian Cells," *Science* 214:916–919 (1981).

Raju et al., "Analysis of Sindbis Virus Promoter Recognition in vivo Using Novel Vectors with Two Subgenomic mRNA Promoters," *J. Virology* 65(5):2501–2510 (1991).

Ratner et al., "Complete Nucleotide Sequence of the AIDS Virus, HTLV–III," *Nature* 313:277–284 (1985).

Reed et al., "Oncogenic Potential of bcl–2 Demonstrated by Gene Transfer," *Nature* 336:259–261 (1988).

Reiss et al., "Newly Systhesized Class II MHC Chains are Required for VSV G Presentation to CTL Clones," *Cellular Immunol.* 139:229–238 (1992).

Rice et al., "Expression of Sindbis Virus Structural Proteins Via Recombinant Vaccinia Virus: Synthesis, Processing, and Incorporation into Mature Sindbis Virions," *J. Virol.* 56(1):227–239 (1985).

Rice et al., "Production of Infectious RNA Transcripts from Sindbis Virus cDNA Clones: Mapping of Lethal Mutations. Rescue of a Temperature–Sensitive Marker and In Vitro Mutagenesis to Generate Defined Mutants," *Journal of Virology* 61(12):3809–3819 (1987).

Rolls et al., "Expression of Additional Genes in a Vector Derived from a Minimal RNA Virus," *Virology* 218:406–411 (1996).

Rolls et al., "Novel Infectious Particles Generated by Expression of the Vesicular Stomatitis Virus Glycoprotein from a Self–Replicating RNA," *Cells* 79(3):497–506 (1994).

Rosenfeld et al., "Adenovirus–Mediated Transfer of Recombinant □1–Antitrypain Genet to the Lung Epithelium in vivo," *Science* 252:431–434 (1991).

Salk et al., "A Strategy for Prophylactic Vaccination Against HIV," *Science* 260:1270–1272 (1993).

Sanchez et al., "Recombinant System for overexpression of Cholera Toxin B Subunit in *Vibrio cholera* as a Basis for Baccine Development," *Proc. Natl. Acad. Sci. U.S.A.* 86:481–485 (Jan. 1989).

Sarver and Stollar, "Sindbis Virus–Induced Cytopathic Effect in Clones of *Aedes albopictus* (Singh) Cells," *Virology* 80:390–400 (1977).

Schlesinger, S., "Alphaviruses–Vectors for the Expression of Heterologous Genes," *Trends Biotechnol.* 11(1):18–22 (1993).

Schlesinger et al., "An In–Frame Insertion into the Sindbis Virus 6K Gene Leads to Defective Paroteolytoc Processing on the Virus Glycoproteins, a Trans–Dominant Negative Inhibitionof Normal Virus Formation, and Interference in Virus Shut Off of Host–Cell Protein Synthesis," *Virology* 193:424–432 (1993).

Schowalter et al., "Heterologous Expression of Adenovirus E3–gp19K in an Ela–deleted Adenovirus Vector Inhibits MHC I Expression in vitro but does not Prolong Transgene Expression in vivo," *Gene Therapy* 4:351–360 (1997).

Searle et al., "The Potential of Carboxypeptidase G2–Antibody Conjugates as Anti–Tumor Agent, I. Preparation of Antihuman Chorionic Gonadotrophin–Carboxypeptidase G2 and Cytotoxicity of the Conjugate Against JAR Choriocarcinoma Cells in vivo," *Br. J. Cancer* 53:377–384 (1986).

Semler et al., "Production of Infectious Poliovirus from Cloned cDNA is Dramatically Increased by SV40 Transcription and Replication Signals," *Nucleic Acids Research* 12(12):5123–5141 (1984).

Shirako and Strauss, "Regulation of Sindbis Virus RNA Replication" Uncleaved P12 and nsP4 funciton in Munus–Strand RNA Synthesis, Whereas Cleaved Products from P123 are Required for Efficient Plus–Strand RNA Synthesis, *J. Virology* 68(3):1874–1885 (1994).

Smerdou et al., "Two–Helper RNA System for Production of Recombinant Semliki forest Virus Particles," *J. Virol.* 73(2):1092–1098 (Feb. 1999).

Stanton et al., "Nucleotide Sequence Comparison of Normal and Translocated Murine c–myc Genes," *Nature* 310:423–425 (Aug. 1984).

Strauss and Strauss, "The Alphaviruses: Gene Expression, Replication, and Evolution," *Microbiological Reviews* 58(3):491–562 (1994).

Strauss et al., "Complete Nucleotide Sequence of the Genomic RNA of Sindbis Virus," *Virology* 133:92–110 (1984).

Strauss et al., "Identification of the Active Site Residues in the nsP2 Proteinase of Sindbis Virus," *Virology* 191:932–940 (1992).

Stirpe et al., "Gelonin, a New Inhibitor of Protein Synthesis, Nontoxic to Intact Cells," *J. Biological Chemistry* 255(14):6947–6953 (1980).

Struck, "Vaccine R & D Success Rates and Development Times," *Nature Biotechnology* 14:591–593 (1996).

Taylor et al., "Sindbis Virus: A Newly Recognized Arthropod–Transmitted Virus," *Ann . J. Trop. Med. Hyg.* 4:844–862 (1955).

Tubulekas et al., "Alphavirus Expression Vectors and Their Use as Recombinant Vaccines: A Minireview," *Gene* 190(1):191–195 (1997).

Tysoe–Calnon et al., "Molecular Comparisons of the Beta 2 Microglobulin Binding Site in Class I Major Histocompatibility Comples Alpha chain and Proteins of Related Sequences," *Biochemistry* 277:359–369 (1991).

Wagner et al, Nucleotide Sequence of the Thymidine Kinase Gene of Herpes Siplex Virus Type 1, *Proc. Natl. Acad. Sci. U.S.A.* 78(3):1441–1445 (Mar. 1981).

Wang et al., "pH–Sensitive Immunoliposomes Midiate Target–Cell–Specific Delivery and Controlled Expression of Foreign Gene in Mouse," *Proc. Natl. Acad. Sci. U.S.A.* 84:7851–7855 (Nov. 1987).

Wang et al., "Antidiotypic Antibodies as Probes for the Sindbis Virus Reception," *Virology* 181:694–702 (1991).

Watson et al., "A Mutant CHO–K1 Strain with Resistance to Pseudomonas Exotoxin A and Alphaviruses Fails to Cleave Sindbis Virus Glycoprotein PE2," *Journal of Virology* 65(5):2332–2339 (1991).

Weiss and Schlesinger, "Recombinant Between Sindbis Virus RNAs," *J. Virol.* 65(8):4017–4025 (1991).

Weiss et al., "Evidence for Specificity in the Encapsidation of Sindbis Virus RNAs," *Journal of Virology* 63:5310–5318 (1989).

Weiss et al., "Interaction Between Sindbis Virus RNAs and a 68 Amino Acid Derivative of the Viral Capsid Protein Further Defines the Capsid Binding Site," *Nucleic Acids Reserch* 22(5):780–786 (1994).

Weiss et al., "Establishment and Maintenance of Persistant Infection by Sindbis Virus in BHK Cells," *J. Virology* 33(1):463–474 (1990).

Weiss and Schlesinger, "Defective Interfering Particles of Sindbis Virus Do Not Interfere with the Homologous Virus Obtained From Persistently Infected BHK Cells but Do Interfere with Semliki Forest Virus," *Journal of Virology* 37(2):840–844 (1981).

Wen and Schlesinger, "Regulated Expression of Sindbis and Vesicular Stomatitis Virus Glycoproteins in *Saccahomyces cerevisiae*," *Proc. Natl. Acad. Sci. U.S.A.* 83:3639–3643 (1986).

Willey et al., "In Vitro Mutagenesis Identifies a Region Within the Envelope Gene of the Human Immunodeficiency Virus that is Critical for Infectivity," *Journal Virology* 62:139–147 (1988).

Williams et al., "Introduction of Foreign Genes into Tissue of Living Mice by DNA–Coated Microprojectiles," *Proc. Natl. Acad. Sci.* 88:2726–2730 (1991).

Wilson et al., "Prospects for Gene Therapy for Familial Hypercholesterolemia," *Mol. Biol. Med.* 7:223–232 (1990).

Wu et al., "Targeting Genes: Delivery and Persistent Expression of a Foreign Gene Driven by Mammalian Regulatory Elements in vivo," *J. Biological Chemistry* 264(20):16985–16987 (1989).

Xiong et al., "Sindbis Virus: An Efficient Broad Host Range Vector for Gene Expression in Animal Cells," *Science* 243(4895):1188–1191 (1989).

Yamamoto et al., "The Human LDL receptor: a Cysteine–Rich Protein with Multiple Alu Sequences in its mRNA," *Cell* 39:27–38 (1984).

Zhang et al., "Cloning of Human IL–12p40 and p35 DNA into the Semliki Forest Virus Vector: Expression of IL–12 Human Tumor Cells," *Gene Therapy* 4(4):367–374 (1997).

Zhou et al., "Self–Replicating Semliki Forest Virus RNA as Recombinant Vaccine," *Vaccine* 12(16):1510–1514 (1994).

Zhou et al., "Generation of Cytotoxic and Humoral Immune Responses by Nonreplicative Recombinant Semliki Forest Virus," *Proc. Natl. Acad. Sci. U.S.A.* 92(7):3009–3013 (1995).

\* cited by examiner

- 6L Thin-film Oxygenator, 2 ft$^2$
- DO$_2$ Probes: Pre & Post Module
- Circulation, 2.0 L/min
- 1/4" ID Ports
- Single 100S Module (85K cm$^2$)

METHOD FOR THE QUANTITATION OF ALPHAVIRUS REPLICON PARTICLES

RELATED APPLICATION

The present application is based on provisional application serial number 60/208376, which was filed on May 31, 2000 and which is incorporated by reference herein.

TECHNICAL FIELD OF THE INVENTION

The present invention relates generally to the purification of viruses and virus-derived vectors, including those related to alphaviruses, from biological and chemical preparations. In particular, this invention relates to methods of purification of such viruses and vectors from preparations by subjecting the preparation to chromatographic purification using an ion exchange resin or combination of an ion exchange resin step and another chromatographic process step such as size exclusion or affinity chromatography. The method provides purified viruses and vectors for use as effective vaccines and therapeutics. Moreover related methods for quantifying replicon vector preparations and verifying the replication incompetency of purified vectors are provided.

BACKGROUND OF THE INVENTION

Alphaviruses comprise a set of genetically, structurally, and serologically related arthropod-borne viruses of the Togaviridae family. Twenty-six known viruses and virus subtypes have been classified within the alphavirus genus, including, Sindbis virus, Semliki Forest virus, Ross River virus, and Venezuelan equine encephalitis virus.

Sindbis virus is the prototype member of the Alphavirus genus of the Togaviridae family. Its replication strategy has been well characterized in a variety of cultured cells and serves as a well-accepted model for other alphaviruses. Briefly, the genome of Sindbis virus (like other alphaviruses) is an approximately 12 kb single-stranded positive-sense RNA molecule which is capped and polyadenylated, and contained within a virus-encoded capsid protein shell. The nucleocapsid is further surrounded by a host-derived lipid envelope into which two viral-specific glycoproteins, E1 and E2, are inserted and anchored to the nucleocapsid. Certain alphaviruses (e.g., SFV) also maintain an additional protein, E3, which is a cleavage product of the E2 precursor protein, PE2.

After virus particle adsorption to target cells, penetration, and uncoating of the nucleocapsid to release viral genomic RNA into the cytoplasm, the replicative process occurs via four alphaviral nonstructural proteins (nsPs), translated from the 5' two-thirds of the viral genome. Synthesis of a full-length negative strand RNA, in turn, provides template for the synthesis of additional positive strand genomic RNA and an abundantly expressed 26 S subgenomic RNA, initiated internally at the junction region promoter. The alphavirus structural proteins (sPs) are translated from the subgenomic 26S RNA, which represents the 3' one-third of the genome, and like the nsPs, are processed post-translationally into the individual proteins.

Several members of the alphavirus genus are being developed as "replicon" expression vectors for use as vaccines and therapeutics. Replicon vectors may be utilized in several formats, including DNA, RNA, and recombinant vector particles. Such replicon vectors have been derived from alphaviruses that include, for example, Sindbis virus (Xiong et al., Science 243:1188–1191,1989; Dubensky et al., J. Virol. 70:508–519,1996; Hariharan et al., J. Virol. 72:950–958, 1988; Polo et al., PNAS 96:4598–4603, 1999), Semliki Forest virus (Liljestrom, Bio/Technology 9:1356–1361, 1991; Berglund et al., Nat. Biotech. 16:562–565, 1998), and Venezuelan equine encephalitis virus (Pushko et al., Virology 239:389–401, 1997). A wide body of literature has now demonstrated efficacy of such replicon vectors for applications such as vaccines (see for example, Dubensky et al., ibid; Berglund et al., ibid; Hariharan et al., ibid, Pushko et al., ibid; Polo et al., ibid; Davis et al., J Virol. 74:371–378, 2000; Schlesinger and Dubensky, Curr Opin. Biotechnol. 10:434–439, 1999; Berglund et al., Vaccine 17:497–507, 1999).

Because of their configuration, vector replicons do not express the alphavirus structural proteins necessary for packaging into recombinant alphavirus particles (replicon particles). Thus, to generate replicon particles, these proteins must be provided in trans. Packaging may be accomplished by a variety of methods, including transient approaches such as co-transfection of in vitro transcribed replicon and defective helper RNA(s) (Liljestrom, Bio/Technology 9:1356–1361, 1991; Bredenbeek et al., J. Virol. 67:6439–6446, 1993; Frolov et al., J. Virol. 71:2819–2829, 1997; Pushko et al., Virology 239:389–401, 1997; U.S. Pat. Nos. 5,789,245 and 5,842,723) or plasmid DNA-based replicon and defective helper constructs (Dubensky et al., J. Virol. 70:508–519, 1996), as well as introduction of alphavirus replicons into stable packaging cell lines (PCL) (Polo et al., PNAS 96:4598–4603, 1999; U.S. Pat. Nos. 5,789,245, 5,842,723, and 6,015,694; PCT publications WO 9738087 and WO 9918226).

Alphavirus replicon particles produced using any of the above methodologies subsequently are harvested in the cell culture supernatants. The replicon particles then may be concentrated and partially purified using one of several published approaches, including polyethylene glycol (PEG) precipitation, ultracentrifugation, or Cellufine sulfate™ ion exchange chromatography. Unfortunately, these methods do not remove a sufficient level of non-alphavirus derived protein contaminants, are not scalable, or are costly, and therefore are likely not amenable for commercial manufacture necessary of vaccine and therapeutic products.

The present invention provides methods of production and purification with utility for the large-scale manufacture of alphavirus replicon particles. Also disclosed are novel methods for quantitating vector particles in a preparation and determining the presence or absence of contaminating replication-competent virus in a preparation. Additional methods are provided for detecting the presence of packaged helper RNAs in a preparation of replicon particles. Alphavirus particles produced and characterized according to the methods described herein may be used for a variety of applications, including for example, vaccines and gene therapy.

SUMMARY OF THE INVENTION

Briefly stated, the present invention provides methods of production and purification for alphavirus replicon particles. Such replicon particles may be derived from a wide variety of alphaviruses (e.g., Semliki Forest virus, Ross River virus, Venezuelan equine encephalitis virus, Sindbis virus), and are designed to express a variety of heterologous proteins (e.g., antigens, immunostimulatory proteins, therapeutic proteins).

Within one aspect of the invention, a method of purifying alphavirus replicon particles is provided. Purification is achieved by first contacting a preparation containing alphavirus replicon particles with an ion exchange resin, under conditions and for a time sufficient to bind to the resin. Next, the portion of the preparation which is not bound to the ion exchange resin is removed from the ion exchange resin, and then the bound alphavirus replicon particles are eluted from the ion exchange resin and recovered. In one embodiment, the ion exchange resin is a tentacle ion exchange resin. In another embodiment, the tentacle ion exchange resin is a cationic exchange resin. In yet another embodiment, the tentacle ion exchange resin is an anionic exchange resin.

Within another aspect of the invention, a method of purification for alphavirus replicon particles is provided, comprising at least two chromatographic purification steps. The chromatographic purification steps are selected from the group consisting of ion exchange chromatography, size exclusion chromatography, hydrophobic interaction chromatography, and affinity chromatography. In one preferred embodiment, purification is performed using a first step of ion exchange chromatography and a second step of size exclusion chromatography.

Within another aspect of the invention, a method of producing alphavirus replicon particles is provided. Alphavirus packaging cells are infected with a seed stock of alphavirus replicon particles and then incubated in a bioreactor, under conditions and for a time sufficient to permit the production of alphavirus replicon particles. Next the culture supernatants containing the replicon particles are harvested. In one embodiment, the bioreactor is an external component bioreactor. In another embodiment the bioreactor is a suspension culture bioreactor.

Within another aspect of the invention, a method of producing alphavirus replicon particles is provided. Alphavirus packaging cells are transfected with a DNA-based alphavirus replicon or eukaryotic layered vector initiation system and then incubated in a bioreactor, under conditions and for a time sufficient to permit the production of alphavirus replicon particles. Next the culture supernatants containing the replicon particles are harvested.

Within another aspect of the invention, a method of producing alphavirus replicon particles is provided wherein alphavirus packaging cells are transfected with an alphavirus RNA vector replicon transcribed in vitro and then incubated in a bioreactor, under conditions and for a time sufficient to permit the production of alphavirus replicon particles. Next the culture supernatants containing the replicon particles are harvested.

Within other aspects of the invention, methods of generating alphavirus replicon particles for use in vaccine or therapeutic applications are provided. Replicon particles are produced in packaging cell lines and purified by a chromatographic purification process as described above. In preferred embodiments, the chromatographic purification process includes a step of ion exchange chromatography using a tentacle ion exchange resin.

Within yet other aspects of the present invention, a preparation of alphavirus replicon particles is provided, wherein the preparation of replicon particles is purified by a chromatographic purification process as described above. In preferred embodiments, the chromatographic purification process includes a step of ion exchange chromatography using a tentacle ion exchange resin.

Within a related aspect, a vaccine or immunogenic composition comprising a preparation of alphavirus replicon particles purified by a chromatographic purification process as described above is provided. The preparation of replicon particles being capable of expressing an antigen derived from a pathogenic agent. In preferred embodiments, the chromatographic purification process includes a step of ion exchange chromatography using a tentacle ion exchange resin. In one embodiment, the antigen is derived from a tumor cell. In another embodiment, the antigen is derived from an infectious agent (e.g., virus, bacteria, fungus, and parasite). In preferred embodiments, the antigen is derived from HIV (e.g. gag, gp120, gp140, gp160, pol, rev, tat, and nef) or HCV (e.g. C, E1, E2, NS3, NS4, and NS5).

Within yet other related aspects, methods for stimulating an immune response within a warm-blooded animal, comprising the step of administering to a warm-blooded animal a preparation of alphavirus replicon particles purified by a chromatographic purification process as described above are provided, the preparation of replicon particles being capable of expressing an antigen derived from a pathogenic agent. In preferred embodiments, the chromatographic purification process includes a step of ion exchange chromatography using a tentacle ion exchange resin. In one embodiment, the antigen is derived from a tumor cell. In another embodiment, the antigen is derived from an infectious agent (e.g., virus, bacteria, fungus, parasite). In preferred embodiments, the antigen is derived from HIV or HCV.

Within yet other related aspects, methods for stimulating an immune response within a warm-blooded animal, comprising the step of administering to a warm-blooded animal a preparation of alphavirus replicon particles purified by a chromatographic purification process as described above are provided, the preparation of replicon particles being capable of expressing a lymphokine, cytokine, or chemokine. In preferred embodiments, the chromatographic purification process includes a step of ion exchange chromatography using a tentacle ion exchange resin. In one embodiment, the lymphokine, cytokine or chemokine is selected from the group consisting of IL-2, IL-10, IL-12, gamma interferon, GM-CSF, MIP3$\alpha$, MIP3$\beta$, and SLC.

Still other embodiments of the present invention provide for techniques used to establish vector particle preparation safety and potency. One important aspect of vector particle safety is that the preparation be free of contaminating replication-competent alphaviral particles. The packaging cell lines used to produce the vector particles of the present invention contain at least three separate nucleic acid sources used to produce the vector particles of the present invention. One nucleic acid source contains nonstructural viral proteins and a gene of interest, another contains genes encoding for structural proteins and a third encodes for structural proteins not present in any other nucleic acid source. Therefore, contaminating replication-competent alphaviral particles can only arise if a minimum of two recombination events occur.

In one embodiment a preparation of replicon particles free from detectable contaminating replication-competent alphaviral particles is assured using polymerase chain reaction (PCR) techniques wherein a nucleic acid substrate suitable for detecting multiple recombination events is provided. The substrate is derived from a population of alphavirus replicon particles and the nucleic acid substrate is reacted with at least one first reaction mixture comprising an oligonucleotide complementary to an alphavirus nonstructural protein gene and an oligonucleotide complementary to an alphavirus structural protein gene. The structural protein gene is either a capsid protein gene or a non-capsid structural protein gene. Suitable reaction conditions and time are provided to permit amplification of the nucleic acid substrate and the formation of a first reaction product. Next, the first reaction product is reacted with a second reaction mixture containing an oligonucleotide complementary to an alphavirus capsid protein gene and an oligonucleotide complementary to a non-capsid alphavirus structural protein gene. Suitable reaction conditions and time are provided to permit amplification of the nucleic acid substrate and the formation of a second reaction product. After the first and second reactions are complete, the presence or absence of the second reaction product is established.

In another embodiment of the present invention multiple recombination events are detected by providing a nucleic acid substrate suitable for detecting multiple recombination events, the substrate being derived from a population of alphavirus replicon particles. Then reacting the nucleic acid substrate with a first reaction mixture comprising an oligonucleotide complementary to an alphavirus nonstructural protein gene and an oligonucleotide complementary to an alphavirus capsid protein gene. Conditions suitable and for a time sufficient to permit amplification of the nucleic acid substrate to form a first reaction product are provided. Next, the first reaction product is reacted with a second reaction mixture comprising an oligonucleotide complementary to an alphavirus capsid protein gene and an oligonucleotide complementary to a non-capsid alphavirus structural protein gene. Again, under conditions suitable and for a time sufficient to permit amplification of the nucleic acid template to form a second reaction product. Finally, determining the presence or absence of the second reaction product In yet another embodiment a method for detecting multiple recombination events is provided comprising providing a nucleic acid substrate suitable for detecting multiple recombination events. The substrate is derived from a population of alphavirus replicon particles and then reacting the nucleic acid substrate with a first reaction mixture comprising an oligonucleotide complementary to an alphavirus nonstructural protein gene and an oligonucleotide complementary to a non-capsid alphavirus structural protein gene. Suitable reaction conditions and time are provided to permit amplification of the nucleic acid substrate to form a first reaction product. Next the first reaction product is reacted with a second reaction mixture comprising an oligonucleotide complementary to an alphavirus capsid protein gene and an oligonucleotide complementary to a non-capsid alphavirus structural protein gene. After a suitable incubation time, the presence or absence of the second reaction product is determined.

In one preferred embodiment, at least two of the above methods for detecting multiple recombination events are performed using the same nucleic acid substrate derived from a population of alphavirus replicon particles.

In another embodiment of the present invention replicon particle preparation potency is quantified. In this embodiment, methods are provided for quantitating or "titering" replication incompetent RNA virus vector particles in a sample. The methods comprising providing a population of packaging cells, contacting the packaging cells with the sample under conditions suitable and for a time sufficient for the cells to be infected with replication-incompetent virus vector particles. Then incubating the infected packaging cells under conditions suitable and for a time sufficient for production of virus vector particles and enumerating the number of resulting plaques.

These and other aspects and embodiments of the invention will become evident upon reference to the following detailed description and attached figures. In addition, various references are set forth herein that describe in more detail certain procedures or compositions (e.g., plasmids, sequences, etc.), and are therefore incorporated by reference in their entirety as if each were individually noted for incorporation.

DEFINITION OF TERMS

Figure 1:
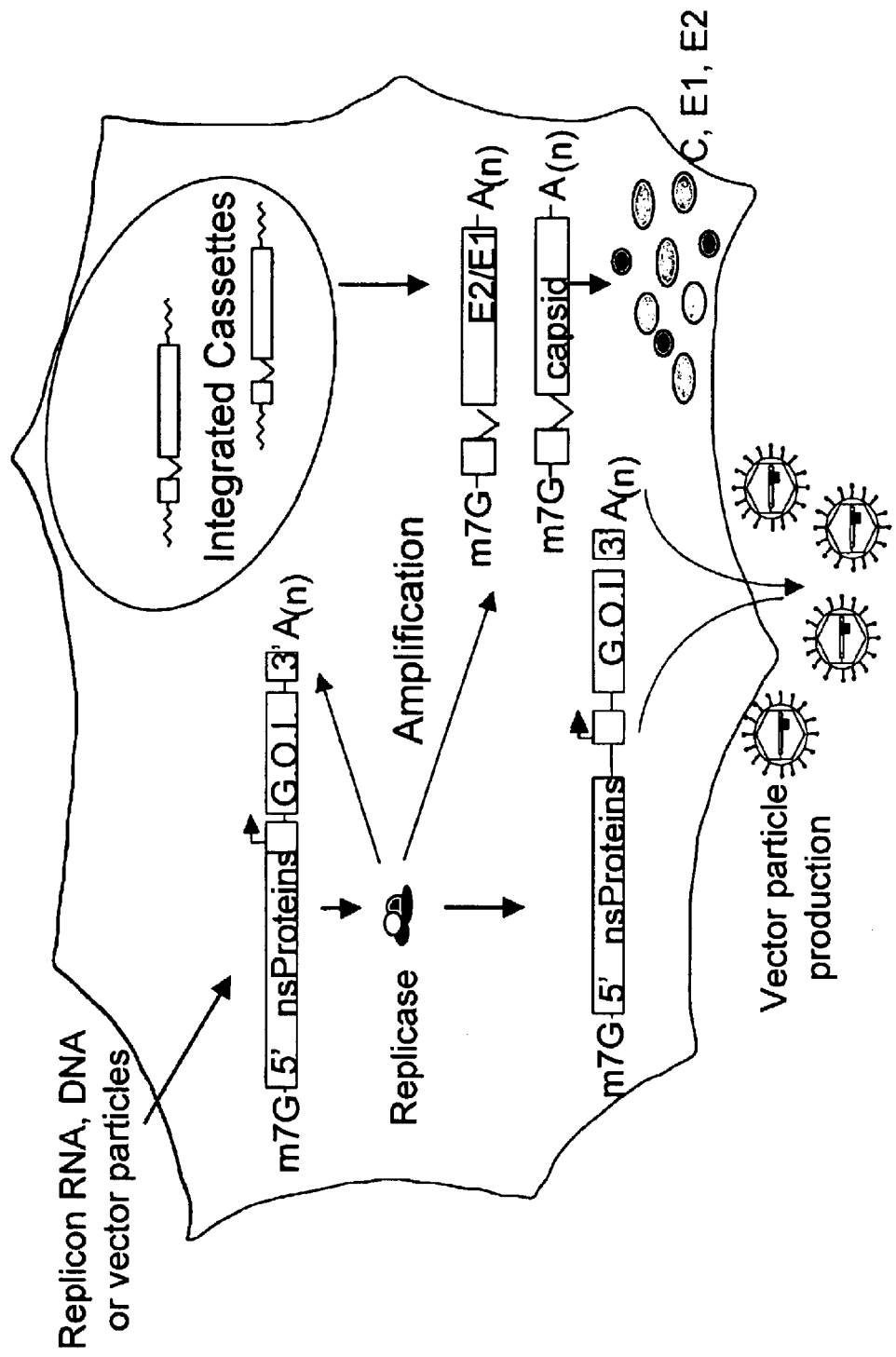
FIG. 1 is a schematic illustration of an alphavirus replicon packaging cell line with a split structural protein gene expression cassette configuration.

The following terms are used throughout the specification. Unless otherwise indicated, these terms are defined as follows:

"Alphavirus RNA vector replicon", "RNA vector replicon" and "replicon" refers to an RNA molecule which is capable of directing its own amplification or self-replication in vivo, within a target cell. To direct its own amplification, the RNA molecule should encode the polymerase(s) necessary to catalyze RNA amplification (e.g., nsP1, nsP2, nsP3, nsP4) and contain cis RNA sequences required for replication which are recognized and utilized by the encoded polymerase(s). An alphavirus RNA vector replicon should contain the following ordered elements: 5' viral sequences required in cis for replication (also referred to as 5° CSE), sequences which, when expressed, code for biologically active alphavirus nonstructural proteins (e.g., nsP1, nsP2, nsP3, nsP4), 3' viral sequences required in cis for replication (also referred to as 3° CSE), and a polyadenylate tract. The alphavirus RNA vector replicon also may contain a viral subgenomic "junction region" promoter, which may, in certain embodiments, be modified in order to increase or reduce viral transcription of the subgenomic fragment, and heterologous sequence(s) to be expressed.

"Recombinant Alphavirus Particle", "Alphavirus replicon particle" and "Replicon particle" refers to a virion unit containing an alphavirus RNA vector replicon. Generally, the recombinant alphavirus particle comprises one or more alphavirus structural proteins, a lipid envelope and an RNA vector replicon. Preferably, the recombinant alphavirus particle contains a nucleocapsid structure that is contained within a host cell-derived lipid bilayer, such as a plasma membrane, in which one or more alphaviral envelope glycoproteins are embedded. The particle may also contain other components (e.g., targeting elements such as biotin, other viral structural proteins, hybrid envelopes, or other receptor binding ligands) which direct the tropism of the particle from which the alphavirus was derived.

"Alphavirus packaging cell line" refers to a cell which contains one or more alphavirus structural protein expression cassettes and which produces recombinant alphavirus particles after introduction of an alphavirus RNA vector replicon, eukaryotic layered vector initiation system, or recombinant alphavirus particle. The parental cell may be of mammalian or non-mammalian origin. Within preferred embodiments, the packaging cell line is stably transformed with the structural protein expression cassette(s).

"Eukaryotic Layered Vector Initiation System" refers to an assembly that is capable of directing the expression of a sequence or gene of interest. The eukaryotic layered vector initiation system should contain a 5' promoter which is capable of initiating in vivo (i.e. within a eukaryotic cell) the synthesis of RNA from cDNA, and a nucleic acid vector sequence (e.g., viral vector) which is capable of directing its own replication in a eukaryotic cell and also expressing a heterologous sequence. Preferably, the nucleic acid vector sequence is an alphavirus-derived sequence and is comprised of a 5' sequence which is capable of initiating transcription of an alphavirus RNA (also referred to as 5' viral sequences required in cis for replication or 5° CSE), as well as sequences which, when expressed, code for biologically active alphavirus nonstructural proteins (e.g., nsP1, nsP2, nsP3, nsP4), and an alphavirus RNA polymerase recognition sequence (also referred to as 3' viral sequences required in cis for replication or 3° CSE). In addition, the vector sequence may include an alphaviral subgenomic "junction region" promoter which may, in certain embodiments, be modified in order to prevent, increase, or reduce viral transcription of the subgenomic fragment, as well as a polyadenylation sequence. The eukaryotic layered vector initiation system may also contain splice recognition sequences, a catalytic ribozyme processing sequence, a nuclear export signal, heterologous gene, and a transcription termination sequence. In certain embodiments, in vivo synthesis of the vector nucleic acid sequence from CDNA may be regulated by the use of an inducible promoter or subgenomic expression may be inducible through the use of translational regulators or modified nonstructural proteins.

"External Component Bioreactor" refers to an integrated modular bioreactor system for the mass culture, growth, and process control of substrate attached cells. The External Component Bioreactor should have a vessel or chamber with tissue culture treated growth surface for attachment and propagation of cells (e.g., alphavirus packaging cells). Unlike traditional "stir-tank" bioreactors, which may have an internal mechanical agitation (e.g., impeller) and/or sparging system to circulate culture media and facilitate gas exchange, the External Component Bioreactor should have external components or modules that are connected (i.e., via tubing), to achieve similar functions. In certain embodiments, the external components may include pumps, reservoirs, oxygenators, culture modules, and other non-standard parts.

"Tentacle ion exchange resin" refers to a resin, gel or matrix with functional charge groups and wherein the functional charge groups are carried by long polymer chains ("tentacles"), rather than being located on the surface of the resin, gel or matrix. In certain embodiments, the tentacle ion exchange resin is a cationic resin, gel or matrix that may be used to bind and fractionate biological substances on the basis of charge characteristics. A representative example of a tentacle cationic exchange resin is Fractogel® EMD $SO_3^-$ (M) (s-Fractogel®). In other embodiments, the tentacle ion exchange resin is an anionic resin, gel or matrix that may be used to bind and fractionate biological substances on the basis of charge characteristics. A representative example of a tentacle anionic exchange resin is Fractogel® EMD DEAE (M).

Numerous aspects and advantages of the invention will be apparent to those skilled in the art upon consideration of the following detailed description, which provides illumination of the practice of the invention.

DETAILED DESCRIPTION OF THE INVENTION

As noted above, the present invention provides methods of purification for viruses and virus-derived vectors, including those related to alphaviruses, from biological and chemical preparations. In particular, this invention relates to methods of purification for such viruses and vectors from preparations by subjecting the preparation to chromatographic purification methods, such as for example, using a tentacle cationic exchange resin with or without a second chromatographic purification step. Viruses and vectors purified according to this invention have use as effective vaccines and therapeutics.

Alphavirus Vector Replicins and Replicin Particles

As noted above, the present invention provides replicons and replicon particles derived from a wide variety of alphaviruses. Such replicons and particles, including sequences encoding alphaviruses suitable for use in preparing the above-described materials, have been described in detail elsewhere (see, for example, U.S. Pat. Nos. 5,789,245, 5,842,723, and 6,015,694; PCT Nos. WO 97/38087, WO 99/18226, WO 00/61772, and WO 00/39318), which are hereby incorporated by reference in their entirety.

Heterologous Sequences

A wide variety of nucleotide sequences may be carried and expressed by the alphavirus replicon particles of the present invention, including, for example, sequences which encode lymphokines, cytokines, or chemokines (e.g., IL-2, IL-12, GM-CSF, SLC), prodrug converting enzymes (e.g., HSV-TK, VZV-TK), antigens which stimulate an immune response (e.g., HIV, HCV, tumor antigens), therapeutic molecules such as growth or regulatory factors (e.g., VEGF, FGF, PDGF, BMP), proteins which assist or inhibit an immune response, as well as ribozymes and antisense sequences. The above nucleotide sequences include those referenced previously (e.g., U.S. Pat. No. 6,015,686, WO 97/38087 and WO 99/18226, WO 00/61772, and WO 00/39318), and may be obtained from repositories, readily cloned from cellular or other RNA using published sequences, or synthesized, for example, on an Applied Biosystems Inc. DNA synthesizer (e.g., APB DNA synthesizer model 392 (Foster City, Calif.)).

Alphavirus Replicon Particle Production

Alphavirus replicon particles according to the present invention may be produced using a variety of published methods. Such methods include, for example, transient packaging approaches, such as the co-transfection of in vitro transcribed replicon and defective helper RNA(s) (Liljestrom, Bio/Technology 9:1356–1361, 1991; Bredenbeek et al., J. Virol. 67:6439–6446, 1993; Frolov et al., J. Virol. 71:2819–2829, 1997; Pushko et al., Virology 239:389–401, 1997; U.S. Pat. Nos. 5,789,245 and 5,842,723) or plasmid DNA-based replicon and defective helper constructs (Dubensky et al., J. Virol. 70:508–519, 1996), as well as introduction of alphavirus replicons into stable packaging cell lines (PCL) (Polo et al., PNAS 96:4598–4603,1999; U.S. Pat. Nos. 5,789,245, 5,842,723, 6,015,694; WO 97/38087, WO 99/18226, WO 00/61772, and WO 00/39318).

It should be noted that the selected method for production of replicon particles should preferably minimize or eliminate the possibility of generating contaminating replication-competent virus (RCV). One such strategy to address this issue of RCV is the use of defective helpers or PCL that contain "split" structural protein expression cassettes (see U.S. Pat. No. 5,789,245). In this context, the alphavirus structural protein genes are segregated into separate expression constructs (e.g., capsid separate from glycoproteins) such that multiple recombination events are required to regenerate a complete complement of structural proteins, which is extremely unlikely.

In preferred embodiments, stable alphavirus packaging cell lines are utilized for replicon particle production (FIG. 1). The PCL may be transfected with in vitro transcribed replicon RNA, transfected with plasmid DNA-based replicon (e.g., ELVIS vector), or infected with a seed stock of replicon particles, and then incubated under conditions and for a time sufficient to produce high titer packaged replicon particles in the culture supernatant. In particularly preferred embodiments, PCL are utilized in a two-step process, wherein as a first step, a seed stock of replicon particles is produced by transfecting the PCL with a plasmid DNA-based replicon. A much larger stock of replicon particles is then produced in the second step, by infecting a fresh culture of the PCL with the seed stock. This infection may be performed using various multiplicities of infection (MOI), including a MOI=0.01, 0.05, 0.1, 0.5, 1.0, 3, 5, or 10. Preferably infection is performed at a low MOI (e.g., less than 1). Replicon particles at titers>$10^8$ infectious units (IU)/ml can be harvested over time from PCL infected with the seed stock. In addition, the replicon particles can subsequently be passaged in yet larger cultures of naïve PCL by repeated low multiplicity infection, resulting in commercial scale preparations with the same high titer. Importantly, by using PCL of the "split" structural gene configuration, these replicon particle stocks are free from detectable contaminating RCV.

As described above, large-scale production of alphavirus replicon particles may be performed using a bioreactor. Preferably, the bioreactor is an External Component Bioreactor, which is an integrated modular bioreactor system for the mass culture, growth, and process control of substrate attached cells. The attachment and propagation of cells (e.g., alphavirus packaging cells) occurs in a vessel or chamber with tissue culture treated surfaces, and the cells are with fresh media for increased cell productivity. Monitoring and adjustments are performed for such parameters as gases, temperature, pH, glucose, etc., and crude vector is harvested using a perfusion pump. Typically, the individual components of an External Bioreactor separate external modules that are connected (i.e., via tubing). The external components can be pumps, reservoirs, oxygenators, culture modules, and other non-standard parts. A representative example of an External Component Bioreactor is the CellCube™ system (Corning, Inc).

In addition to using the External Component Bioreactor described herein, a more traditional Stir Tank Bioreactor may also be used, in certain instances, for alphavirus replicon particle production. In a Stir Tank Bioreactor, the alphavirus packaging cells may be unattached to any matrix (i.e., floating in suspension) or attached to a matrix (e.g., poly disks, micro- or macro carriers, beads). Alternatively, a Hollow Fiber Culture System may be used.

Purification Using Ion Exchange Resins

Following harvest, crude culture supernatants containing the alphavirus replicon particles may be clarified by passing the harvest through a filter (e.g., 0.2 uM, 0.45 uM, 0.65 uM, 0.8 uM pore size). Optionally, the crude supernatants may be subjected to low speed centrifugation prior to filtration to remove large cell debris. Within one embodiment, an endonuclease (e.g., Benzonase, Sigma #E8263) is added to the preparation of alphavirus replicon particles before or after a chromatographic purification step to digest exogenous nucleic acid. Further, the preparation may be concentrated prior to purification using one of any widely known methods (e.g., tangential flow filtration).

Crude or clarified alphavirus replicon particles may be concentrated and purified by chromatographic techniques (e.g., ion exchange chromatography, size exclusion chromatography, hydrophobic interaction chromatography, affinity chromatography). Two or more such purification methods may be performed sequentially. In preferred embodiments, at least one step of ion exchange chromatography is performed and utilizes a tentacle ion exchange resin. Briefly, clarified alphavirus replicon particle filtrates may be loaded onto a column containing a charged ion exchange matrix or resin (e.g., cation or anion exchange). The matrix or resin may consist of a variety of substances, including but not limited to cross linked agarose, cross linked polystyrene, cross linked styrene, hydrophilic polyether resin, acrylic resin, and methacrylate based resin. The ion exchanger component may comprise, but is not limited to, a cationic exchanger selected from the list consisting of sulphopropyl cation exchanger, a carboxymethyl cation exchanger, a sulfonic acid exchanger, a methyl sulfonate cation exchanger, and an SO3-exchanger. In other embodiments, the ion exchanger component may comprise, but is not limited to, an anionic exchanger selected from the list consisting of DEAE, TMAE, and DMAE. Most preferably, ion exchange chromatography is performed using a tentacle cationic exchanger, wherein the ion exchange resin is a methacrylate-based resin with an SO3-cation exchanger (e.g., Fractogel® EDM SO3-).

The replicon particles may be bound to the ion exchange resin followed by one or more washes with buffer containing a salt (e.g., 250 mM or less NaCl). Replicon particles then may be eluted from the column in purified form using a buffer with increased salt concentration. In preferred embodiments, the salt concentration is a least 300 mM, 350 mM, 400 mM, 450 mM or 500 mM. Elution may be monitored preferably by a spectrophotometer at 280 nm, but also by replicon titer assay, transfer of expression (TOE) assay, or protein gel analysis with subsequent Coomassie staining or Western blotting.

The higher salt elution buffer subsequently may be exchanged for a more desirable buffer, for example, by dilution in the appropriate aqueous solution or by passing the particle-containing eluate over a molecular exclusion column. Additionally, the use of a molecular size exclusion column may also provide, in certain instances, further purification. For example, in one embodiment Sephacryl S-500 or S-400 (Pharmacia) chromatography may be used as both a buffer exchange as well as to further purify the fractions containing the replicon particles eluted from an ion exchange column. Using this particular resin, the replicon particles generally are eluted in the late void volume and show improvement in the level of purity as some of the contaminants are smaller in molecular weight and are retained on the column longer. However, alternative resins of different compositions as well as size exclusion could also be used that might yield similar or improved results. In these strategies, larger-sized resins such as Sephacryl S-1000 could be incorporated that would allow the replicon particles to enter into the matrix and thus be retained longer, allowing fractionation.

Methods of Determining Replicon Particle Titer

Two methods of titering alphavirus replicon particles are widely accepted in the viral vector field. The first method of titering is a simple transfer of expression assay, wherein a culture of naïve cells is infected with various dilutions (e.g., serial dilutions) of the unknown replicon particle preparation and individual cells expressing the encoded gene of interest are quantitated to arrive at original titer. Identification of cells expressing the encoded gene of interest may be performed according to the specific protein being expressed (e.g., fluorescence for GFP reporter, chemical staining for β-gal, immunocytochemistry for proteins with available antibody). Alternatively, an alphavirus reporter cell line (e.g., Olivo et al., Virology 198:381–384, 1984) may be used in conjunction with replicon particles expressing a reporter gene, which serve as a known titer standard curve. Values for the unknown, obtained after infection of the reporter cell line with various dilutions, can be extrapolated to calculate titer.

The present invention discloses additional methods of quantitating replicon particles in a preparation, and these methods are not limited on a preparation by preparation basis, such as from one gene of interest to another. The first method is based upon nucleic acid detection and amplification of the nucleic acid product or a signal that is specific to the assay. Such methods can include, for example, PCR, ™A and bDNA (branched DNA) assays. These nucleic acid based assays provide extremely sensitive levels of detection. More specifically, in the case of a bDNA based assay, a single-stranded DNA probe that is specific and unique to a region of alphavirus genomic and replicon RNA was designed. This probe is bound to the bDNA plate. Target cells that have been infected with serial dilutions of replicon particle preparations are lysed and directly transferred to the bDNA plate. After overnight incubation, the alphavirus genomic RNA hybridizes to the homologous single-stranded DNA probe. The plate is then washed to clear non-specific material, and sequentially incubated with a series of hybridization amplifiers. The signal generated is luminescence-based and can be analyzed in a spectrophotometer. A standard curve can be generated using reporter replicon particle preparations of known titer, for example vector encoding β-galactosidase or green fluorescent protein. The titer of the unknown sample is determined by extrapolation.

The second method of quantitation is by complementation of the replicon vector so as to allow detection by plaque assay in cultured cells. Replication defective viral vectors, such as alphavirus replicons, which are deleted of one or more genes encoding structural proteins necessary for packaging are considered "suicide vectors" and cannot spread from cell to cell. As such, traditional plaque assay methods of quantitation are impossible. The present invention provides a method of performing plaque assay by using packaging cells which express the necessary structural proteins required for production of progeny particles. The packaging cells used for such an assay may contain one or more structural protein expression cassettes. In the case of alphavirus replicon particles, packaging cells are infected with serial dilutions of replicon particle preparations, overlayed and plaques enumerated.

Pharmaceutical Compositions

As noted above, the present invention also provides pharmaceutical compositions comprising purified alphavirus replicon particles in combination with a pharmaceutically acceptable carrier, diluent, or recipient. As used herein, purified shall mean an alphavirus replicon particle preparation free from detectable non-alphavirus proteins. Dectection of non-alphavirus proteins is determined by gel electrophoresis using a sample size of between approximately $10^8$ to $10^9$ replicon particles. Gel electrophoreiss methods including, but not limited to polyacrylamide gel electrophoresis (PAGE), disc electrophoresis and SDS-PAGE, followed by standard Coomassie staining. More specifically, "purified" shall mean alphavirus particle preparations subjected to multi-step chromatography purification procedures as disclosed herein. Within certain preferred embodiments, a sufficient amount of formulation buffer is added to the purified replicon particles to form an aqueous suspension. In preferred embodiments, the formulation buffer comprises a saccharide and a buffering component in water, and may also contain one or more amino acids or a high molecular weight structural additive. The formulation buffer is added in sufficient amount to reach a desired final concentration of the constituents and to minimally dilute the replicon particles. The aqueous suspension may then be stored, preferably at −70° C., or immediately dried.

The aqueous suspension can be dried by lyophilization or evaporation at ambient temperature. Briefly, lyophilization involves the steps of cooling the aqueous suspension below the gas transition temperature or below the eutectic point temperature of the aqueous suspension, and removing water from the cooled suspension by sublimation to form a lyophilized replicon particle. Within one embodiment, aliquots of the formulated recombinant virus are placed into an Edwards Refrigerated Chamber (3 shelf RC3S unit) attached to a freeze dryer (Supermodulyo 12 K). A multistep freeze drying procedure as described by Phillips et al. (Cryobiology 18:414, 1981) is used to lyophilize the formulated replicon particles, preferably from a temperature of −40° C. to −45° C. The resulting composition contains less than 10% water by weight of the lyophilized replicon particles. Once lyophilized, the replicon particles are stable and may be stored at −20° C. to 25° C., as discussed in more detail below. In the evaporative method, water is removed from the aqueous suspension at ambient temperature by evaporation. Within one embodiment, water is removed by a spray-drying process, wherein the aqueous suspension is delivered into a flow of preheated gas, usually which results in the water rapidly evaporating from droplets of the suspension. Once dehydrated, the recombinant virus is stable and may be stored at −20° C. to 25° C.

The aqueous solutions used for formulation preferably comprise a saccharide, a buffering component, and water. The solution may also include one or more amino acids and a high molecular weight structural additive. This combination of components acts to preserve the activity of the replicon particles upon freezing and also lyophilization or drying through evaporation. Although a preferred saccharide is lactose, other saccharides may be used, such as sucrose, mannitol, glucose, trehalose, inositol, fructose, maltose or galactose. A particularly preferred concentration of lactose is 3%–4% by weight.

The high molecular weight structural additive aids in preventing particle aggregation during freezing and provides structural support in the lyophilized or dried state. Within the context of the present invention, structural additives are considered to be of "high molecular weight" if they are greater than 5000 M.W. A preferred high molecular weight structural additive is human serum albumin. However, other substances may also be used, such as hydroxyethyl-cellulose, hydroxymethyl-cellulose, dextran, cellulose, gelatin, or povidone. A particularly preferred concentration of human serum albumin is 0.1% by weight.

The buffering component acts to buffer the solution by maintaining a relatively constant pH. A variety of buffers may be used, depending on the pH range desired, preferably between 7.0 and 7.8. Suitable buffers include phosphate buffer and citrate buffer. In addition, it is preferable that the aqueous solution contains a neutral salt that is used to adjust the final formulated replicon particles to an appropriate iso-osmotic salt concentration. Suitable neutral salts include sodium chloride, potassium chloride or magnesium chloride. A preferred salt is sodium chloride. The lyophilized or dehydrated replicon particles of the present invention may be reconstituted using a variety of substances, but are preferably reconstituted using water. In certain instances, dilute salt solutions that bring the final formulation to isotonicity may also be used.

Methods for Delivery of Replicon Particles

As noted above, the present invention also provides methods for delivering a selected heterologous sequence to a warm-blooded mammal (e.g., a mammal such as a human or other warm-blooded animal such as a horse, cow, pig, sheep, dog, cat, rat or mouse) for use as a vaccine or therapeutic, comprising the step of administering to the mammal replicon particles purified and/or characterized as described herein. Delivery may be by a variety of routes (e.g., intravenously, intramuscularly, intradermally, intraperitoneally, subcutaneously, orally, intraocularly, intranasally, rectally, intratumorally). In addition, the replicon particles may either be administered directly (i.e., in vivo), or to cells which have been removed (ex vivo), and subsequently returned to the warm-blooded mammal.

The following examples are included to more fully illustrate the present invention. Additionally, these examples provide preferred embodiments of the invention and are not meant to limit the scope thereof.

EXAMPLES

Example 1

Production of Alphavirus Replicon Particles Using a Packaging Cell Line

Figure 2:
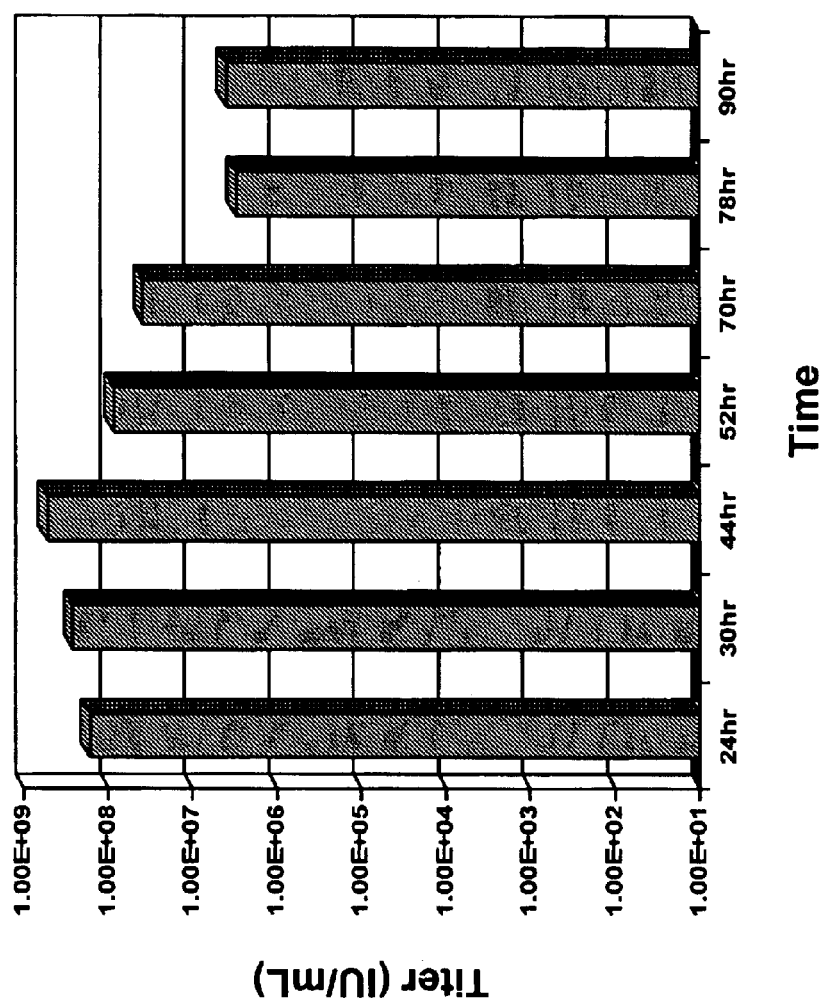
FIG. 2 is a graph showing the production of alphavirus replicon particles using packaging cell line #15–25, in a 10 layer Cell Factory.

To demonstrate scalability of replicon particle production in adherent cultures of an alphavirus packaging cell line, experiments were performed in either a 10-tray Nunc Cell Factory or a Corning Cell Cube. For example, $2.5 \times 10^8$ cells of an alphavirus packaging cell line, PCL #15.25, which expresses human dendritic cell tropic Sindbis structural proteins (Gardner et al., J. Virol., 74:11849–11857, 2000) were suspended in 100 ml of Dulbecco's Modified Eagle's Medium (DMEM) supplemented with penicillin, streptomycin, L-glutamine, and 1% fetal calf serum (FCS). To this suspension, $1.26 \times 10^8$ SIN replicon particles encoding a GFP reporter (Gardner et al., 2000, ibid) were added at a multiplicity of infection (MOI) of approximately 0.57 particles per cell. The suspension was incubated at 37° C. and gently mixed every 15 minutes for approximately 1.5 hours. The suspension was then added to 1 liter of pre-warmed (37° C.) DMEM with 5% FCS, transferred to a 10-tray Nunc Cell Factory, and placed in an incubator set at 34° C., 5% $CO_2$. Complete media exchanges were made at 22 hr, 30 hr, 44 hr, 52 hr, 70 hr, 78 hr, and 90 hr post-infection and replicon particle titers were determined for each harvest (FIG. 2). Culture fluids collected for the highest titer harvests (harvests 1–5) were pooled, transferred to centrifuge bottles, and cell debris was pelleted by centrifugation at 2,500 RPM in a Sorvall RT6000centrifuge, at 4° C. for 15 minutes. The supernatant then was passed through a 0.2 um cellulose acetate filtration unit and used for chromatographic purification as described in example 2 below. Similar production runs have been performed using more than one Cell Factory, in order to increase the total harvest of alphavirus replicon particles proportionally.

Figure 3:
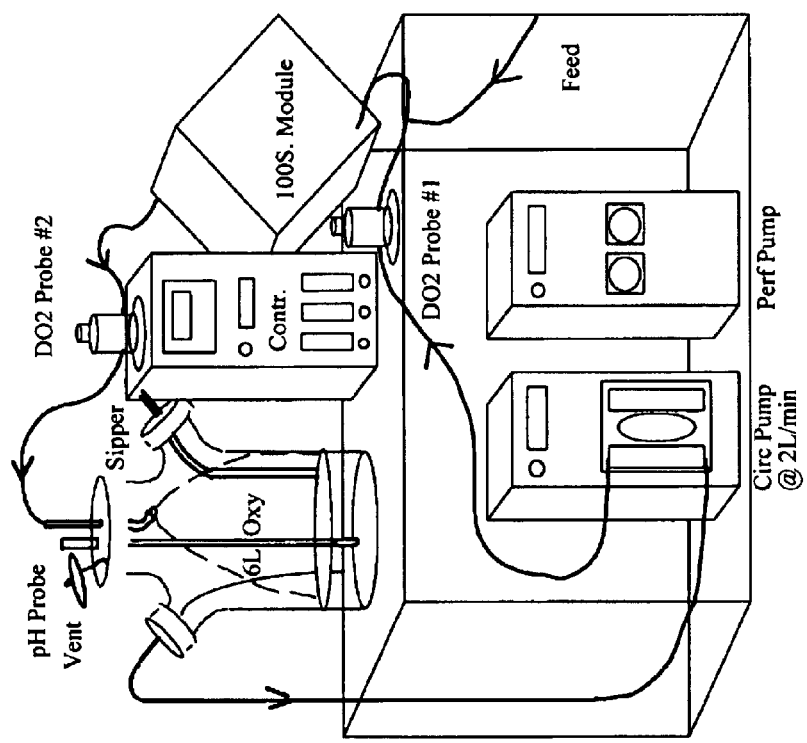
FIG. 3 is a schematic illustration of a CellCube™ bioreactor system

Large-scale manufacture of alphavirus replicon particles also may be accomplished, for example, using the CellCube™ bioreactor system (FIG. 3). The CellCube™ system is an integrated modular bioreactor with multi-layer (100-stack) growth chambers of 85,000 $cm^2$ surface area. Controlling the mixtures of oxygen, $CO_2$ and air allows precise control of pH and $DO_2$ parameters. Together with glucose monitoring and adjustment, this level of culture control provides an increased capacity for replicon particle production.

PCL-based production runs of alphavirus replicon particles using the CellCube™ system requires the input of an initial seed stock of replicon particles to be amplified. To demonstrate feasibility of this approach, CellCube™ production was performed by expanding PCL successively in T225 $cm^2$ cell culture flasks, and increasing to a surface area of four 10-layer Cell Factories prior to suspension infection with the particle seed stock. The PCL were trypsinized using a minimal amount of trypsin, diluted with growth media and then centrifuged briefly. Resuspended cells were counted, split into equal halves, and infected with the seed stock of replicon particles at low MOI infection. Infection was allowed to proceed in suspension with gentle agitation for 30 minutes. After 30 minutes, one vessel was placed on ice and the other was transferred into the inoculation carboy containing 7L of 5% FBS DMEM inoculation media. The 7L of infected cell suspension was transferred into the CellCube and the culture module was rotated 90° to enable the cells to attach. After 60 minutes, the suspension was drained back into the inoculation carboy and the second vial of infected PCL (from ice) was added. This suspension, like the first, was transferred into the culture module, which was then rotated 180° to enable these cells to attach to the opposite side of the culture support plates. After 3 hours, the system was rotated back to the horizontal position and back-filled with 5% DMEM, 20 mM HEPES, after which, circulation was initiated, and gasses were adjusted to maintain pH and DO2 levels. Daily sampling allowed testing and profiling of metabolic indicators including glucose levels. The perfusion system was adjusted based on glucose consumption and previous data to ensure maximum yield of vector. Automated and continuous harvest into 4° C. vessels was used to minimize temperature-induced degradation of replicon particles and allow maximum yield and highest ratio of viable replicon particles.

Figure 4:
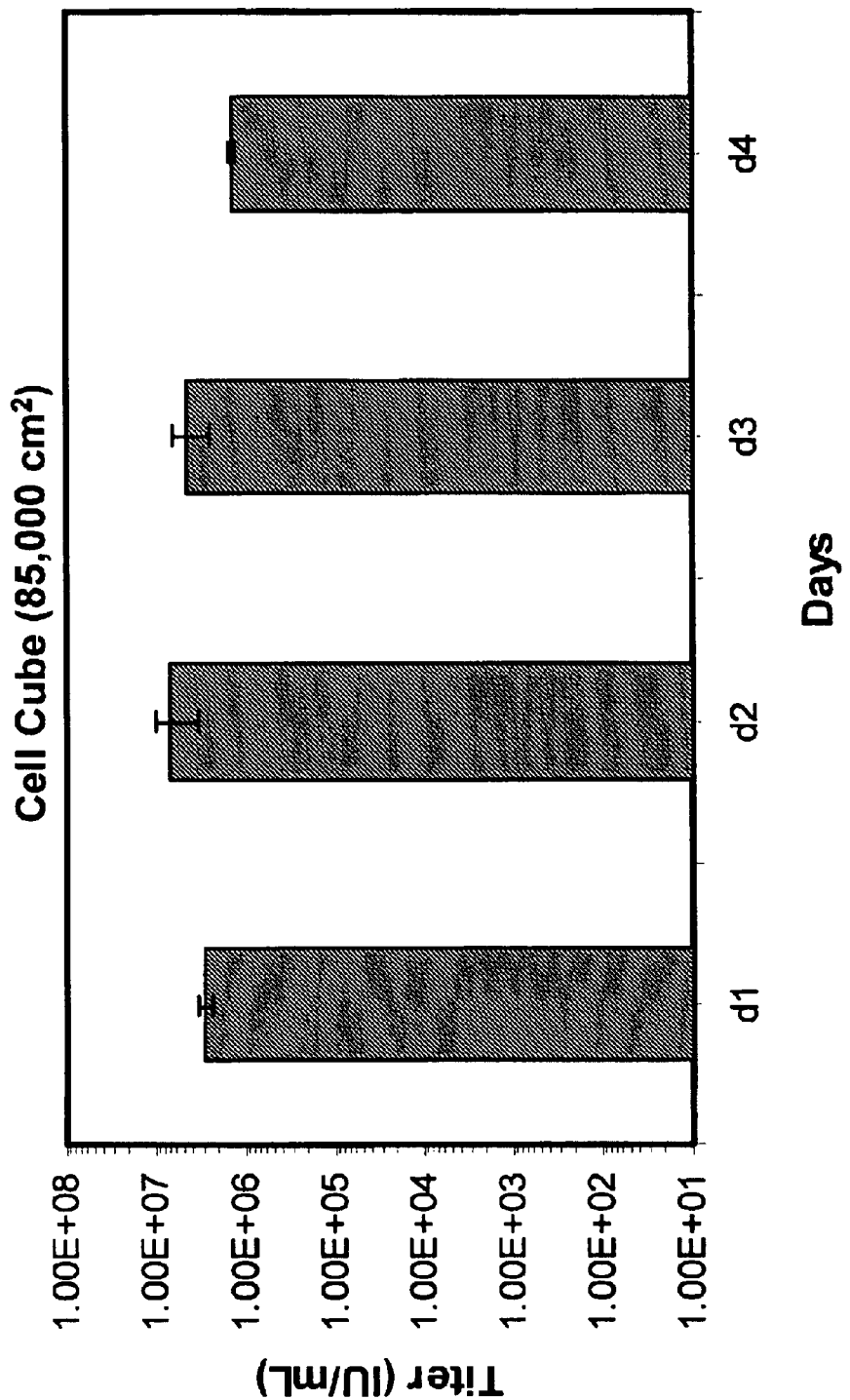
FIG. 4 is a graph showing the scale-up production of 90 liters of alphavirus replicon particles using early generation packaging cell lines in a 100-stack CellCube™ system.

The initial CellCube™ production runs illustrated for this example were performed using early generation replicon and packaging cell lines (prior to the derivation of PCL #15–25 above). These earlier versions of reagents are known to yield alphavirus replicon particles at lower titers (Polo et al., 1999, PNAS 96:4598–4603) than the reagents now available, however such techniques are identical to those that would be used for any subsequently derived vector replicon and packaging cell line. The data obtained using these reagents indicate that large-scale (90–100 liter) production lots can be generated in a 100-stack CellCube™ module, with the same titer efficiency as small, research-scale packaging experiments (FIG. 4). Expanded CellCube™ systems that employ four 100-stack modules, thus, have the potential to readily produce 400L+of replicon particle production material per run.

To generate seed stocks of alphavirus replicon particles without a prior step of in vitro transcription, the packaging cell lines may be transfected with a plasmid DNA-based replicon (Eukaryotic Layered Vector Initiation System) encoding the heterologous gene of interest. Large-scale transfections are carried out in Nunc 10 layer Cell Factories, using the calcium phosphate method according to the following parameters. Packaging cells are plated in the Cell Factory one day prior to transfection at a density of $8 \times 10^4$ cells/$cm^2$. The DNA:calcium phosphate mixture is prepared in a volume of 200 ml, diluted with 1 liter of media and added to the packaging cell line in the Cell Factory. The media is exchanged after 6–8 hr and replicon particle seed stock material is harvested in multiple batches, over a period of 2–3 days. Harvests are pooled, purified, and aliquoted for long-term storage at −80° C. Alphavirus replicon particle seed stock material then may be used for subsequent large-scale amplifications in naïve PCL (e.g., in CellCube bioreactor). Alternative methods of transfecting the plasmid DNA-based replicon also may be substituted readily by one of skill in the art, including but not limited to lipid-mediated transfection and electroporation.

Example 2

Purification of Replicon Particles Using S-Fractogel® Cationic Exchange Resin

To compare the efficiency of replicon particle purification using a tentacle cationic exchange resin, Fractogel® EMD $SO_3^-$ (M) (s-Fractogel®, EM Industries), with the ion exchange resin Matrix® Cellufine™ Sulfate (Amicon), columns of the same size were equilibrated with 10 mM sodium phoshate, 125 mM sodium chloride, pH 7.0. Clarified culture supernatants (~260 ml) containing SIN-GFP replicon particles generated as described (Polo et al., PNAS 96:4598–4603, 1999) were passed through s-Fractogel® and Cellufine™ Sulfate columns at flow rates of 115 and 75 cm/hour respectively. The columns were washed with approximately 20–40 column volumes of buffer containing 10 mM sodium phoshate, 250 mM sodium chloride, pH 7.0, and bound SIN-GFP replicon particles were eluted in a 20 ml, 0.5M–2.0 M NaCl linear gradient collected in 1 ml fractions. A final 3 M NaCl rise was then used to remove any remaining replicon particles.

Figure 5:
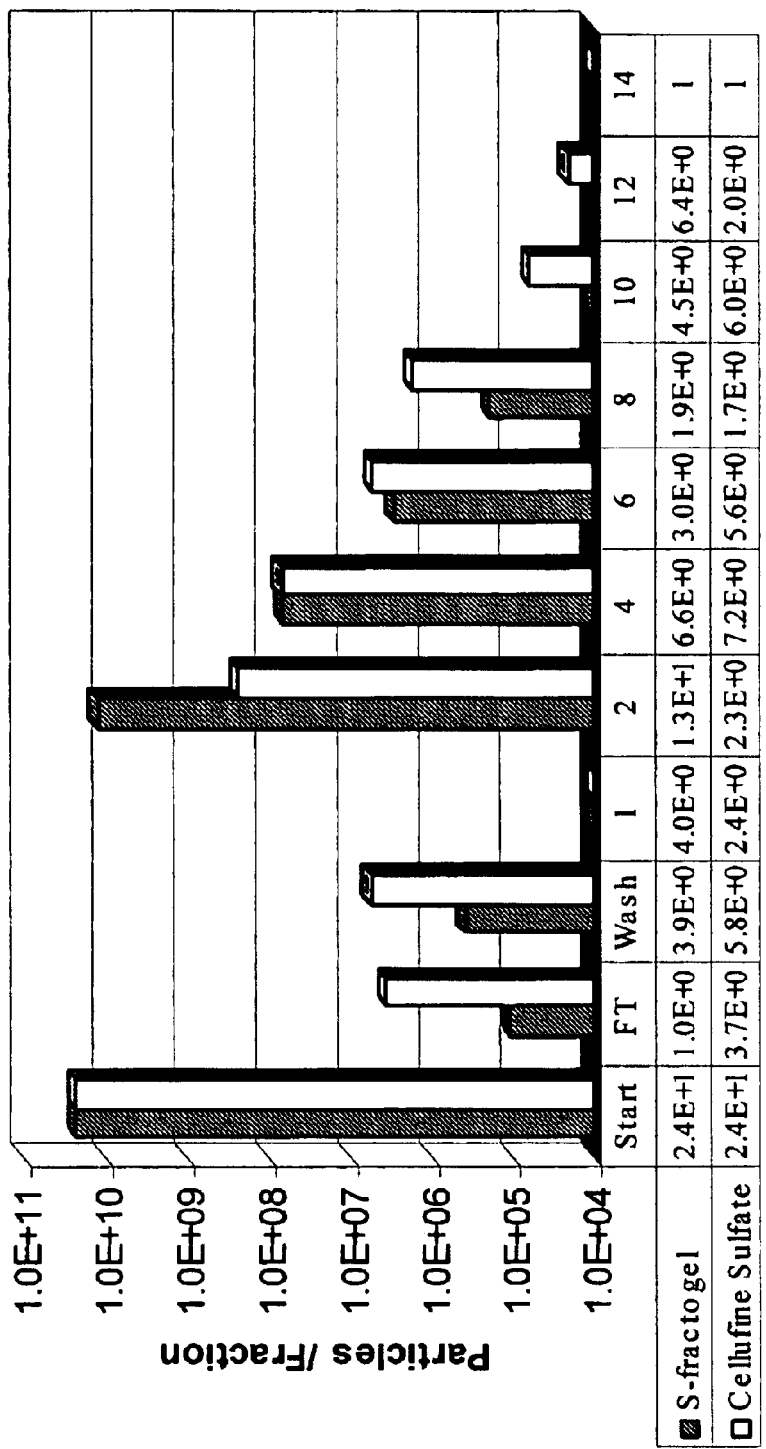
FIG. 5 is a graph comparing the purification of alphavirus replicon particles using two different single-step methods of ion exchange chromatography.

For analysis, consecutive fractions were pooled in pairs starting with fractions 2 and 3, continuing with 4 and 5, etc. Replicon particle titers (total IU) were determined for the recovered fractions, as well as the starting material, load, and wash (FIG. 5). Based on the titer assay results, the 260 ml of clarified supernatant starting material contained approximately $2.4 \times 10^{10}$ IU total. Recovery in the main elution peaks from the s-Fractogel® column was $1.3 \times 10^{10}$ IU total, or approximately 55% of the load, with almost all (99%) concentrated in pooled fractions 2 and 3. Subsequent purification runs using s-Fractogel indicated an average recovery of 80–90%. In contrast, the total recovery from the Cellufine™ Sulfate column was consistently lower, and for this experiment was approximately $3.0 \times 10^8$ IU total (or <2%) in the two main fractions, thus resulting in a considerably more dilute product.

Figure 6:
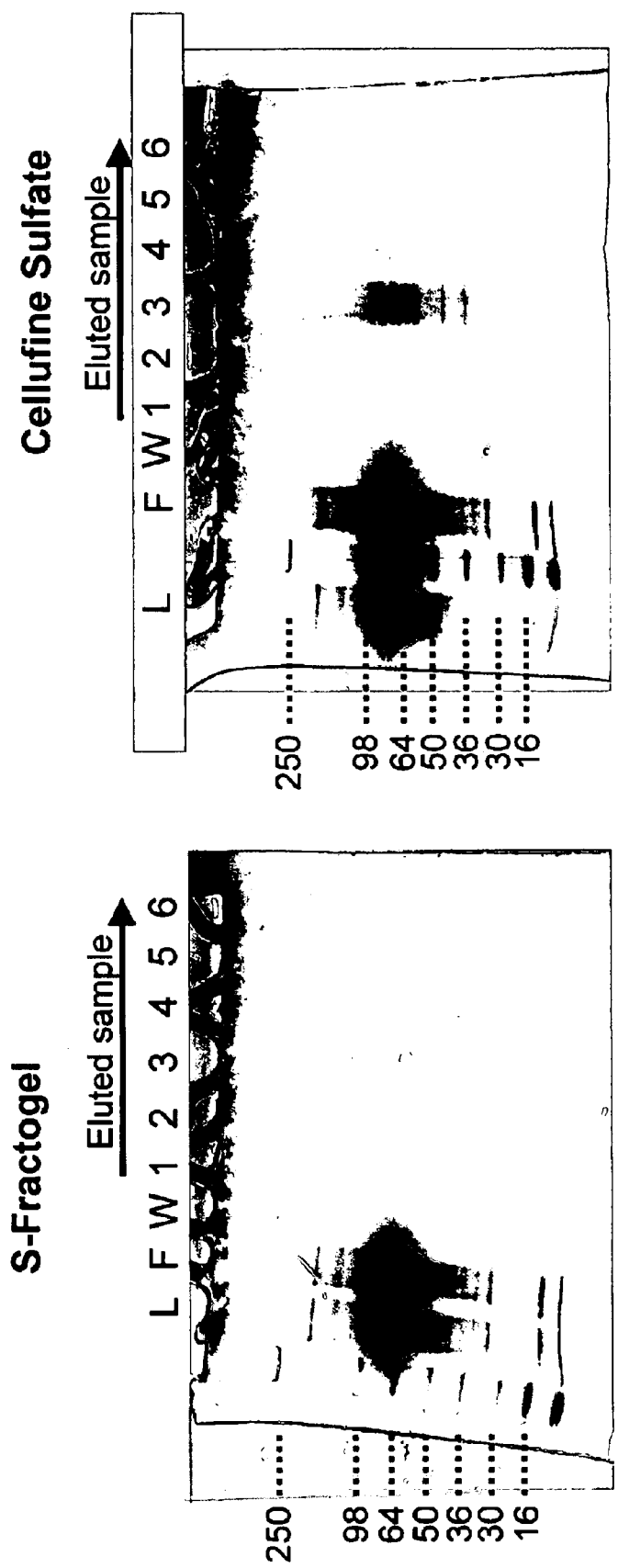
FIG. 6 are Coomassie stained protein gels comparing the purification of alphavirus replicon particles using two different single-step methods of ion exchange chromatography.

Samples also were analyzed for purity by subjecting the collected fractions to polyacrylamide gel electrophoresis (Coomassie staining, FIG. 6) and Western blotting (not shown). The results of 10–20% SDS PAGE Coomassie-stained gels indicated an improvement in the purity of the s-Fractogel® peak as compared to the Cellufine™ Sulfate peak (see SIN particle capsid and glycoprotein bands in sample 2). Interestingly, the main peak of recovered particles, found in pooled fractions 2 and 3 from each column, eluted just prior to a considerable peak of contaminants in pooled fraction 4 and 5 from each column. If fraction ⅘ material was excluded from the Cellufine™ Sulfate pooled products due to the increased amount of impurity, it would reduce the effective recovery even further.

In addition to the improved efficiency of purification, the cost basis of the s-Fractogel® considerably lower than for the Cellufine™ Sulfate. Cost analysis for the resin component only indicates an approximately 3-fold cost decrease with s-Fractogel®, assuming that equal amount of resins could be used. However, the data suggest that there may have been an overloading on the Cellufine™ Sulfate column and that additional resin may be required for equivalent binding capacity. Finally, the reduced flow rate of the Cellufine™ Sulfate column would translate to 50% increase in column run time and thus, another increased cost per run. Taken together, the s-Fractogel® purification method of the present invention provides superior overall utility for large-scale commercial manufacture of alphavirus replicon particles.

In additional experiments, increased volumes of alphavirus replicon particles (e.g., those generated using at least a Cell Factory) also were purified using the s-Fractogel® methodology. For example, a total 25 ml of s-Fractogel® was packed in a Pharmacia AK-26 column and equilibrated with 20 column volumes of buffer (10 mM sodium phosphate, pH 7.0 and 125 mM NaCl) at a linear flow rate of 115 cm/hour. After equilibration, approximately 5.5 liters of culture supernatant containing alphavirus replicon (see Example 1) was passed over the column. The column was washed with approximately 300 ml of wash buffer (10 mM sodium phosphate, pH7.0, 250 mM NaCl), and the particles were eluted in 12 ml fractions by buffer containing 10 mM sodium phosphate, pH7.0, 400 mM NaCl.

Figure 7:
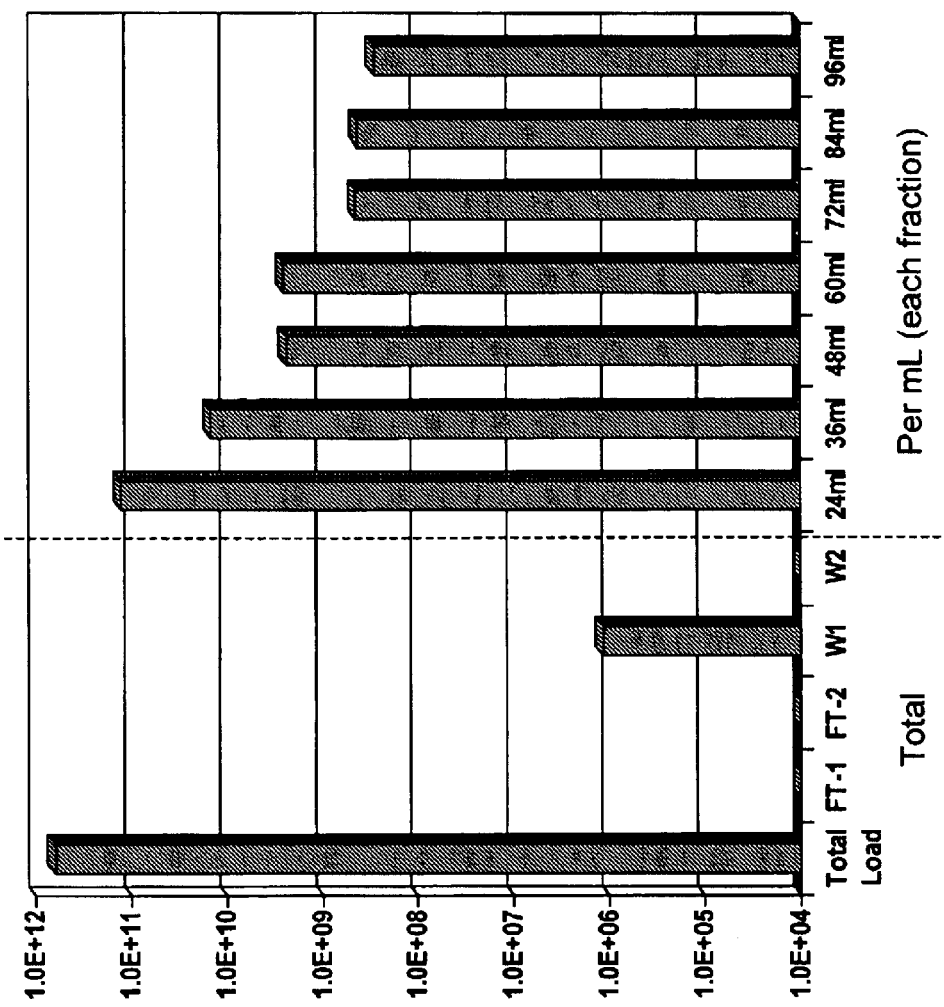
FIG. 7 is a graph showing the purification of alphavirus replicon particles using the tentacle cationic exchange resin s-Fractogel®.

Determination of recovery and identification of peak fractions containing the alphavirus replicon particles was performed by titer assay in which aliquots from the starting material, the flow through, the wash, and the eluted fractions were serially diluted and used to infect BHK-21 cells. The results from this purification procedure (FIG. 7) indicate that the 5.5 liters of harvested supernatant contained replicon particles with a titer of approximately $1.2 \times 10^8$ IU/ml and that only a negligible amount of particles was found in either the flow through or the wash. The highest concentration of eluted, purified particles was found in the $2^{nd}$ and $3^{rd}$ fractions eluted from the column at a concentration of $1.3 \times 10^{11}$ and $1.4 \times 10^{10}$ IU/ml.

Example 3

Stimulation of the Immune Response Using Alphavirus Replicon Particles

To demonstrate the potent stimulation of antigen specific immune responses using purified alphavirus replicon particles, the sequence encoding HIV-1 p55gag was inserted into SIN-based replicons. The HIV gag coding sequence was selected from the HIV-1SF2 strain (Sanchez-Pescador, R., et al., Science 227(4686):484–492, 1985; Luciw, P. A., et al., U.S. Pat. No. 5,156,949, herein incorporated by reference; Luciw, P. A., et al., U.S. Pat. No. 5,688,688). These sequences have been used directly or first manipulated to maximize expression of their gene products. For maximization of expression, the HIV-1codon usage pattern was modified so that the resulting nucleic acid coding sequence was comparable to codon usage found in highly expressed human genes. The HIV codon usage reflects a high content of the nucleotides A or T as third base of the codon-triplet. The effect of the HIV-1 codon usage is a high AT content in the DNA sequence that could result in a decreased translation ability and instability of the mRNA. In comparison, highly expressed human codons prefer the nucleotides G or C as the third base. The gag coding sequence therefore was modified to be comparable to codon usage found in highly expressed human genes.

The DNA fragment for gag first was cloned into the eukaryotic expression vector pCMVKm2, derived from pCMV6a (Chapman et al., Nuc. Acids Res. 19:3979–3986, 1991), to generate the construct pCMVKm2.GagMod.SF2. This plasmid was deposited Jan. 18, 1999, with the Chiron Corporation Master Culture Collection, Emeryville, Calif., 94662-8097, and with the American Type Culture Collection, 10801 University Boulevard, Manassas, Va. 20110-2209. The HIV gag gene then was subcloned into a SIN replicon vector (SINCR, Gardner et al., ibid) for the generation of alphavirus replicon particles by digestion with EcoRI, blunt-ending with Klenow and dNTPs, purification with GeneCleanil, and digestion with SalI. The HIV gag-coding fragment then was ligated into the SINCR vector that had been digested with NotI, blunt-ended, and digested with XhoI. The resulting vector was designated SINCR-gag.

Figure 8:
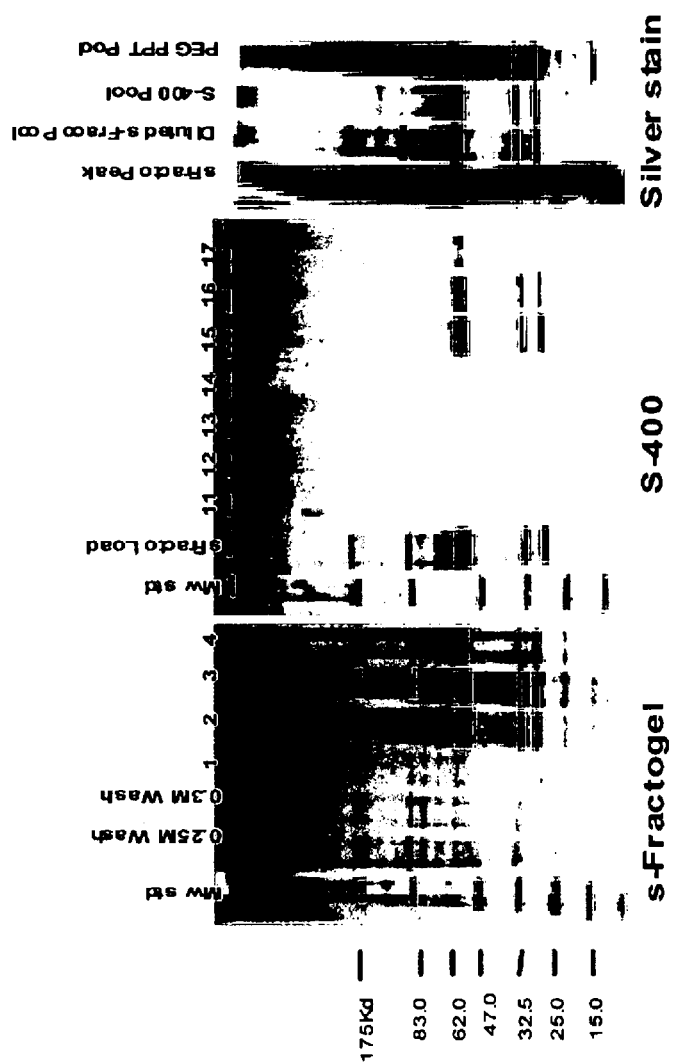
FIG. 8 are Coomassie and silver stained protein gels showing the purification of alphavirus replicon particles using a two step chromatographic process.

To compare the effective purification as well as demonstrate the maintenance of immunogenicity of column-purified replicon particles, a production run of 4×10-tray Nunc Cell Factories was undertaken. Approximately $2 \times 10^9$ cells of alphavirus packaging cell line, PCL #15.25, were suspended in 400 ml of Dulbecco's Modified Eagle's Medium (DMEM) supplemented with penicillin, streptomycin, L-glutamine, and 1% fetal calf serum (FCS). To this suspension, $1 \times 10^{10}$ SIN replicon particles encoding HIV p55 Gag were added at a multiplicity of infection (MOI) of approximately 5. The suspension was incubated at 37° C. and gently mixed every 15 minutes for approximately 1 hour. The suspension was then divided into 4×100 ml aliquots and each 100 ml aliquot was added to 1 liter of pre-warmed (37° C.) DMEM with 5% FCS, transferred to the 10-tray Nunc Cell Factory, and placed in an incubator set at 34° C., 5% $CO_2$. Complete media exchanges were made at 20 hr, 28 hr, and 40 hr post-infection. Culture fluids collected from at each harvest was transferred to centrifuge bottles, and cell debris was pelleted by centrifugation at 2,500 RPM in a Sorvall RT6000 centrifuge, at 4° C. for 15 minutes and the resulting supernatant was passed through a 0.2, um cellulose acetate filtration unit. Approximately 8 L of supernatant was loaded onto a 2.6 cm diameter column containing 30 ml of s-Fractogel resin equilibrated with 10 mM sodium phoshate, 125 mM sodium chloride, pH 7.0. The flow rate of 58 cm/hour was used for the first 5 liters and 115 cm/hour for the last 3 L. The column was rinsed with 10 mM sodium phosphate, 125 mM sodium chloride, pH 7.0 and was followed by two wash steps containing 10 mM sodium phosphate, 250 mM sodium chloride, pH 7.0 then 10 mM sodium phosphate, 300 mM sodium chloride. The particles were eluted with 10 mM sodium phosphate, 400 mM sodium chloride, pH 7.0. The two peak s-Fractogel fractions (#2 and #3) were pooled and 10 ml of the pool was loaded onto a Sephacryl S-400 HR (Pharmacia) (diameter= 2.6 cm, column volume=490 ml) equilibrated with buffer containing 40 mg/ml lactose in PBS. The flow rate was 3.3 ml/minute and each fraction contained 12 ml. Samples from the s-Fractogel and the S-400 were analyzed for titer recovery as well as purity by as determined by polyacrylamide gel electrophoresis Coomassie and silver staining. Based on the titer assay, the 4-cell factory run generated approximately $1 \times 10^{12}$ IU total particles. Approximately $8 \times 10^{11}$ IU were loaded onto the s-Fractogel column and approximately $6 \times 10^{11}$ IU were eluted in the main peak yielding a 75% recovery. From the s-Fractogel peak, $3 \times 10^{11}$ IU were loaded onto the S-400 column, with approximately $1.5 \times 10^{11}$ IU eluted in the main peak resulting in a 50% recovery. The relative purity of the s-Fractogel and the S-400 samples are shown in FIG. 8.

In order to determine if the purified SIN replicon particles encoding HIV-p55 maintained immunogenicity, a study was designed to compare the purified particles with an essentially unpurified, but concentrated (polyethelyene glycol precipitation) preparation of particles using an Gag-specific IFN-γ ELISPOT. In the study, mice (5 mice per group) were immunized with SIN-gag replicon particle preparations ($10^6$ IU/animal) that were PEG precipitated, purified with a single step of cationic exchange chromatography, or a two step process of cationic exchange chromatography followed by size exclusion chromatography. Animals received immunizations at days 0 and 21 with sample collection at days 29 and 30.

To measure the number of Gag-specific IFN-γ secreting cells, an ELISPOT assay was performed. Single-cell suspensions from pooled cervical lymph nodes and spleens from the mice in each group were added onto nitrocellulose or pvdf plates (Millipore) pre-coated with monoclonal rat anti-mouse anti-IFN-γ antibody (Pharmingen) and blocked with complete RPMI medium at pH 7.2, containing 10% fetal calf serum, 5 mM Hepes, and antibiotics. Following overnight incubation of cells in the presence of gag-derived p7g peptide, or anti-CD3 (Pharmingen) and anti-CD28 (Pharmingen) as positive control for polyclonal T cell activation, or media only as negative control, the plates were washed and biotinylated anti-IFN-? (Pharmingen) was added in PBS/0.1% BSA/0.02% Tween and incubated at RIT for 2 hours. The plates were washed with P/T and incubated for 1 hr at 37° C. with Avidin-peroxidase (Pharmingen) at 1:1000 dilution. The plates were washed with P/T and the spots were visualized by adding DAB in Tris-HCI (pH 7.5) buffer for 30 minutes. The plates were washed with de-ionized $H_2O$ and air-dried. Background spots from negative control (media only) wells were subtracted from wells activated with gag-p7g peptide. The number of spots in positive control wells (polyclonally activated with anti-CD3 and anti-CD28) was 5–10 fold higher than the number of spots in wells activated with gag-p7g peptide. The spots were counted with an in-house developed automated ELISPOT reader using software from Alpha Innotech Corporation (San Leandro, Calif.).

Figure 9:
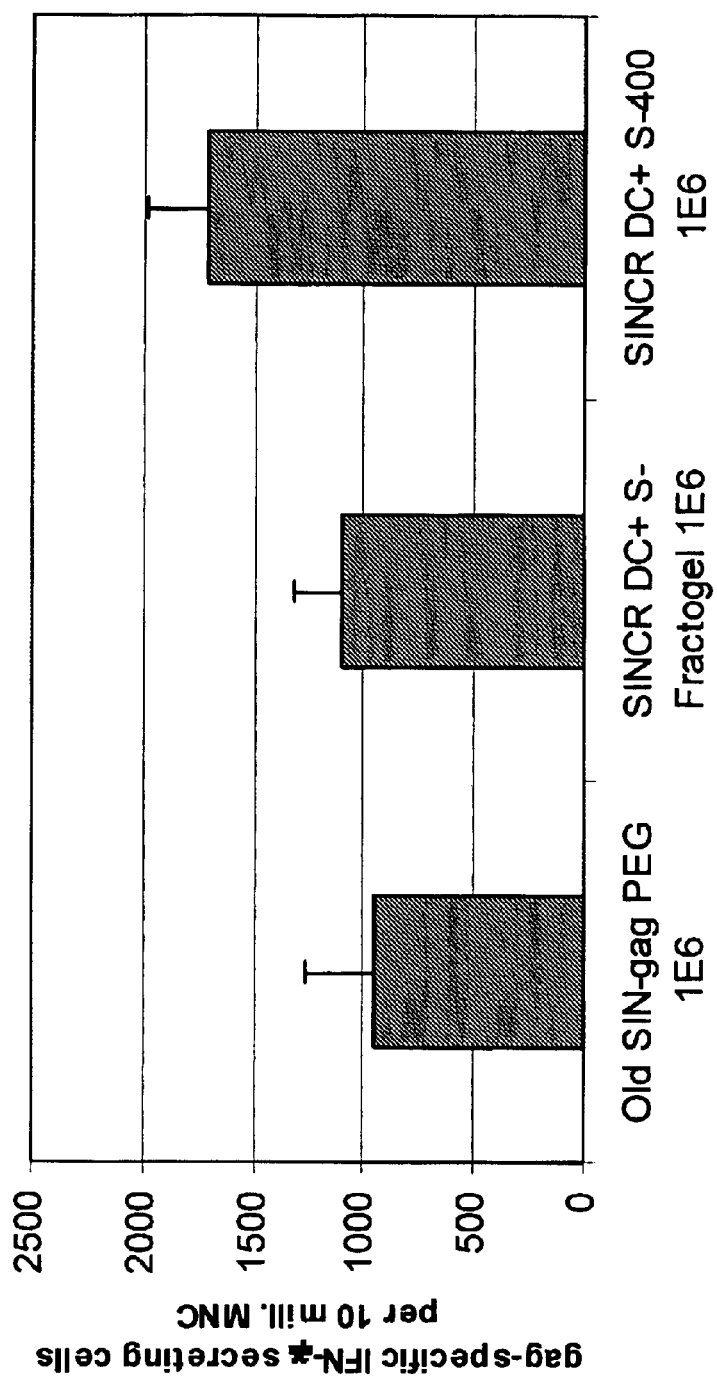
FIG. 9 is a graph showing the induction of HIV gag antigen specific T cells using alphavirus replicon particles subjected to PEG precipitation or single-step Fractogel chromatographic purification or two-step Fractogel/S-400 chromatographic purification.

The results shown in FIG. 9 are representative of two independent experiments from two pools of each group expressed as the number of gag-p7g peptide-specific IFN-γ secreting cells per $10^7$ mononuclear cells. The results indicate no loss of immunogenicity from either method of purification.

Figure 10:
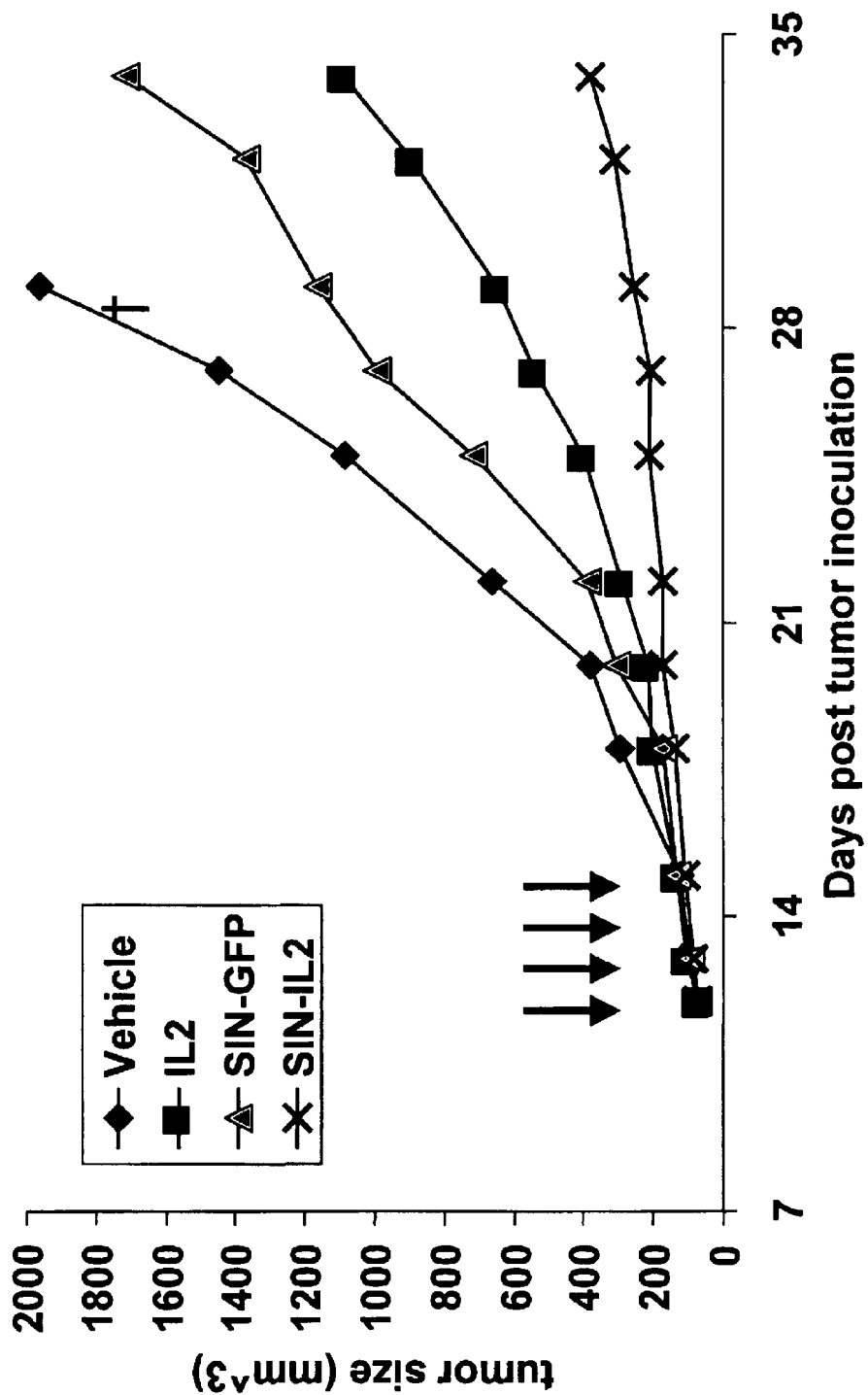
FIG. 10 is a graph showing the anti-tumor effect of SIN alphavirus replicon particles expressing IL2 in a CT26 colon carcinoma model, as compared to recombinant IL-2 protein or SIN replicon particles expressing GFP reporter.

Similarly, the stimulation of an antitumor response was demonstrated in the widely accepted CT26 colon carcinoma system by administering SIN derived alphavirus replicon particles expressing the cytokine IL-2. The IL-2 gene was inserted into the SIN replicon vector following PCR amplification and replicon particles were produced using methods described above. On four successive days following tumor inoculation, mice were injected intratumorally with $10^8$ SIN-IL2 replicon particles. Additional animals received as controls the diluent only, recombinant IL2 protein which has an established clinical efficacy in humans, or SIN-GFP particles. Animals were monitored for increased tumor volume and group means for each treatment group arm were compared. When the group mean for a given arm (e.g., diluent control) reached 2000 mm$^3$, the animals were euthanized compared. As seen in FIG. 10, SIN-IL2 treated animals showed a significant anti-tumor response that was at least comparable to the recombinant IL2 protein.

Example 4

Characterization of Alphavirus Replicon Particles

To quantitate the number of replicon particles in a preparation, two novel methods are disclosed herein. In the first instance, stable alphavirus packaging cell lines (see for example U.S. Pat. No. 5,789,245, U.S. Pat. No. 5,843,723, and WO 99/18226) are provided. The packaging cell lines express each of the alphavirus structural proteins (e.g., capsid, glycoproteins) necessary for production of alphavirus particles, which are not encoded by an alphavirus replicon vector itself. Packaging cell line #15–25 (see above) cells were plated in 6-well dishes to achieve approximately 80–90% confluency at the time of infection. Serial dilutions of a preparation of SIN replicon particles expressing a reporter gene were then diluted serially and used to infect the cells in duplicate, at 37 C for 1 hour. Subsequently, the inoculum was removed, the wells overlayed with agarose and the infected cells incubated at 37 C. Plaques were visualized 48–72 hours later at which time they could be quantitated directly or after staining with a dye such as neutral red or crystal violet.

Figure 11:
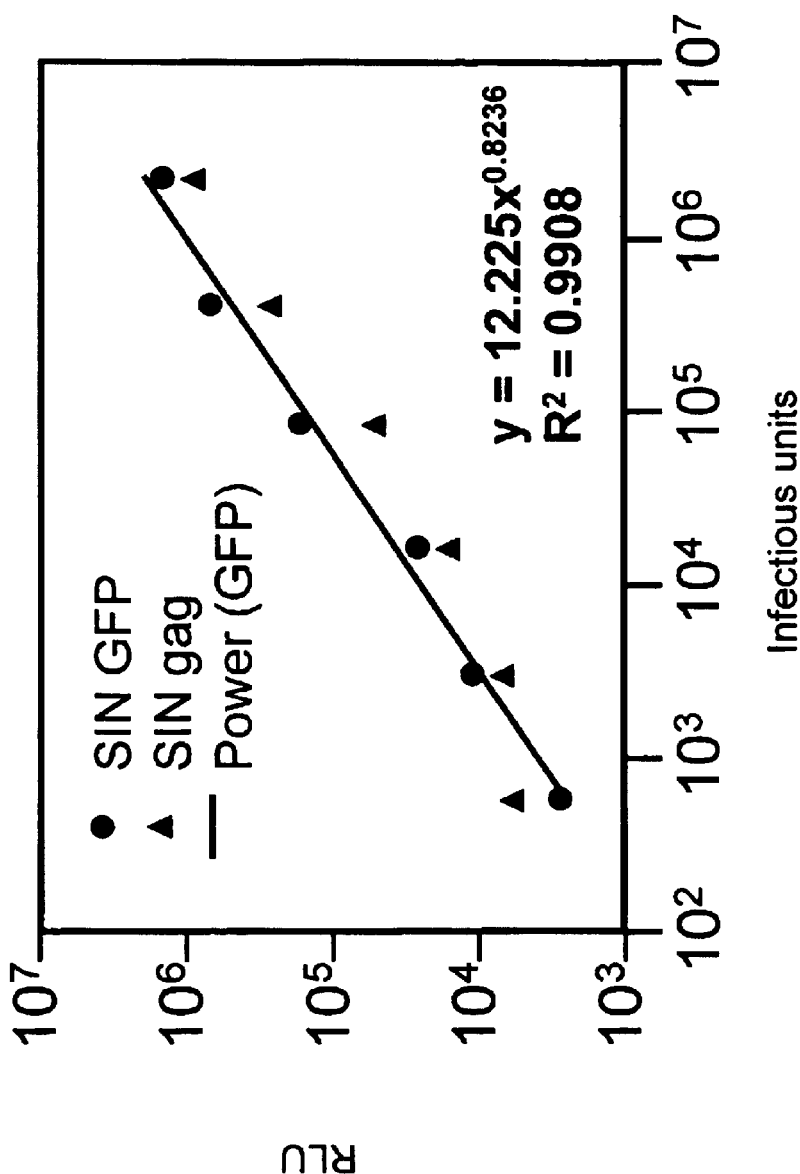
FIG. 11 is a graph showing the use of bDNA assay for detection and quantitation of replicon RNA in a preparation of alphavirus replicon particles as a means to determine titer.

In the second instance, nucleic acid based detection of alphavirus replicon particles as a means for quantitation was performed, using the bDNA amplification technique (Wilber, Immunol Invest 1997, 26:9–13) as one embodiment. FIG. 11 shows representative data from an experiment in which the titer of SIN replicon particles expressing HIV-gag antigen was determined. A standard curve was developed initially using serial dilutions of SIN replicon particles expressing GFP reporter, since prior quantitation of this material could be done by direct transfer of expression (TOE) assay and counting of green cells in a fluorescence microscope. As the vector replicon backbone was identical between SIN-GFP and SIN-gag, nucleic acid detection could then be done using an identical nonstructural gene specific probe, since both particle preparations differed only in the expressed heterologous gene.

Figure 12:
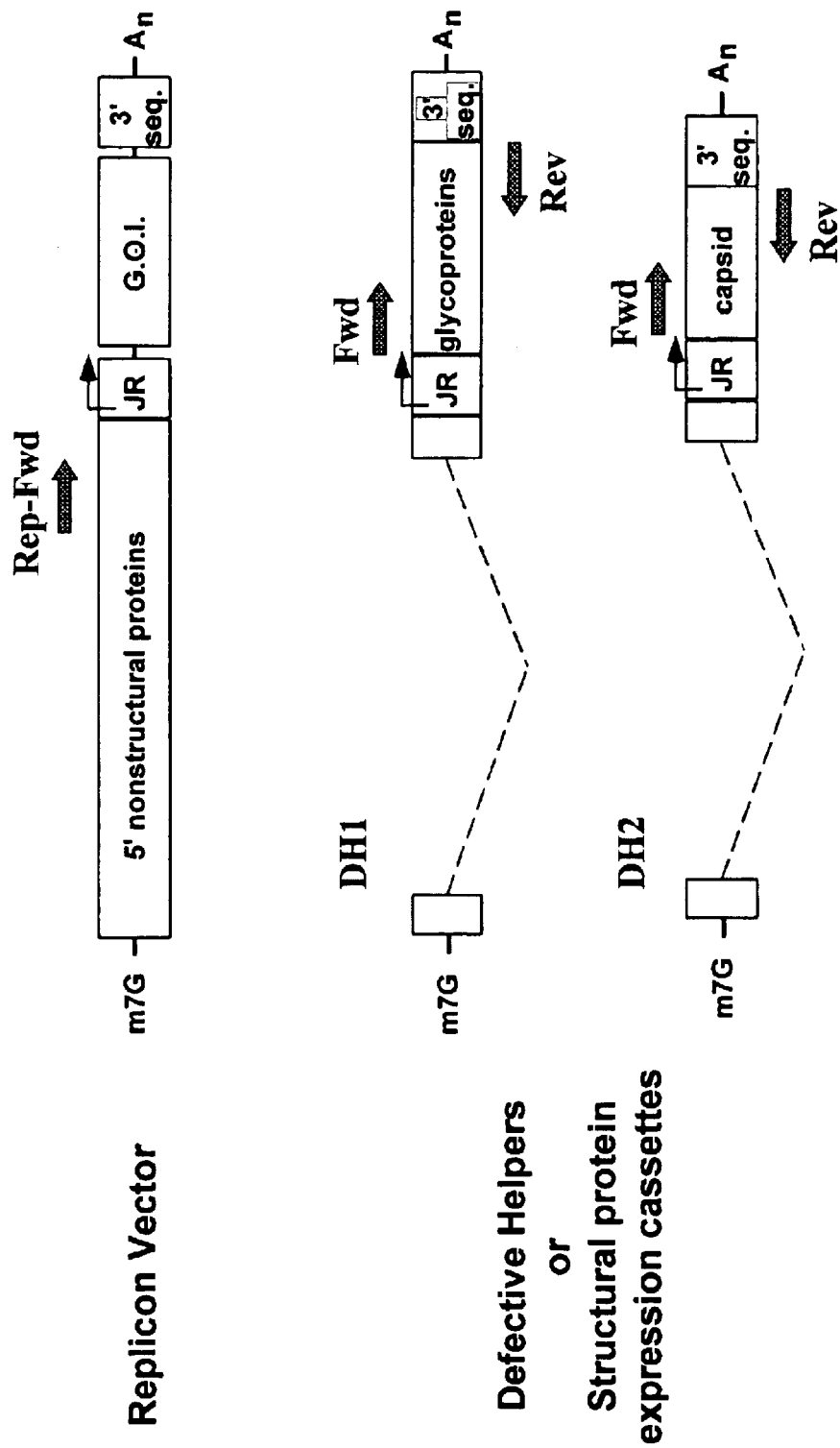
FIG. 12 is a schematic illustration of a method for detection of multiple recombination events using nucleic acid amplification to determine the presence or absence of contaminating replication-competent virus in a preparation of alphavirus replicon particles

In addition to quantifying the number of replicon particles in a preparation, it is also advantageous (or necessary) to determine the presence or absence of contaminating replication-competent virus (RCV) in the preparation. Such RCV, if present, would have resulted from RNA recombination during the replicon packaging process. It has long been recognized by those of skill in the art that RCV testing may be performed using standard plaque assay, with or without prior serial passage in naïve cultured cells. In order to increase the level of sensitivity of RCV detection and to detect the multiple recombination events required for the generation of RCV in a "split helper" alphavirus packaging system, a nucleic acid based assay as described herein has been developed (FIG. 12). In this assay, a preparation containing replicon particles is first extracted to isolate the nucleic acid substrate (e.g., RNA) present. The nucleic acid substrate is then included in a first PCR reaction mixture comprising a first oligonucleotide complementary to an alphavirus sequence not present in the helper sequence(s) (e.g., nonstructural protein gene-specific, Rep-Fwd in FIG. 12), and a second oligonucleotide complementary to an alphavirus structural protein gene (e.g., DH1 Rev or DH2 Rev, in FIG. 12), wherein the structural protein is either a capsid protein or a non-capsid structural protein (e.g., glycoprotein). A reaction product from this reaction will specifically identify a recombination event between the replicon vector and whichever structural protein gene containing helper the second oligonucleotide was designed complementary to. Thus, for example, if the second oligonucleotide was capsid gene-specific oligonucleotide DH2 Rev, a recombination event between the replicon and the capsid gene-containing helper (e.g., DH2) could be detected by the reaction product. In addition, based on length of the reaction product, multiple recombination events might also be detected at this stage, but one could not necessarily ascertain whether such recombination events included all structural gene elements required for generation of RCV or simply recombination with multiple copies of the same structural protein gene helper (e.g., two copies of capsid from DH2).

Therefore, following amplification, the reaction product (s) from the first reaction mixture is included in a second PCR reaction mixture comprising an oligonucleotide complementary to an alphavirus capsid protein gene (e.g., DH2 Rev) and a oligonucleotide complementary to a non-capsid (e.g., glycoprotein) alphavirus structural protein gene (e.g., DH1 Fwd). For example, if the first reaction resulted in a product that was amplified using replicon and capsid specific oligonucleotides (e.g., Rep-Fwd and DH2 Rev), indicating recombination between replicon RNA and capsid-containing helper RNA, then the ability to synthesize a second reaction product in a second reaction containing the first reaction product as template and oligonucleotides complementary to an alphavirus capsid gene E(e.g., DH2 Rev) and non-capsid structural protein gene (e.g., DH1 Fwd), would be indicative of multiple recombination events.

Preferably, two separate first reactions are performed to identify either a capsid gene recombinant (e.g., using Rep-Fwd and DH2 Rev) or a non-capsid structural protein gene recombinant (e.g., using Rep-Fwd and DH1 Rev). Each of these first reactions then would be subjected to a second reaction as described above, allowing for the identification of all possible multiple recombination events that could result in RCV.

Similarly, such an approach may be used to identify packaging of a defective helper RNA into particles within a preparation, as well as co-packaging of replicon and defective helper RNA within particles. For example, the ability to amplify either capsid gene (e.g., DH2 Fwd plus DH2 Rev) or non-capsid structural protein gene (e.g., DH1 Fwd plus DH1 Rev) sequences, without being able to amplify a product resulting from recombination (e.g., Rep-Fwd plus DH1 Rev or DH2 Rev) would be indicative of helper RNA present in packaged particles.

All references including publications, patent applications and patents cited herein are hereby incorporated by reference to the same extent as if each reference was individually and specifically indicated to be incorporated by reference and were set forth in its entirety herein.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for quantitating replication defective alphavirus replicon particles comprising:
    a) providing a population of packaging cells, wherein all structural proteins necessary for production of progeny of replication defective alphavirus replicon particles are expressed in said packaging cells;
    b) contacting said packaging cells with said replication defective alphavirus replicon particles under conditions suitable and for a time sufficient for said cells to be infected with said replication defective alphavirus replicon particles;
    c) incubating said infected packaging cells under conditions suitable and for a time sufficient for production of progeny of said replication defective alphavirus replicon particles;
    d) enumerating the number of resulting plaques, thereby quantitating said replication defective alphavirus replicon particles.

2. The method according to claim 1, wherein said packaging cells comprise at least one expression cassette expressing an alphavirus capsid protein and at least one alphavirus glycoprotein.

3. The method according to claim 1, wherein said packaging cells express an alphavirus capsid protein and at least one alphavirus glycoprotein from distinct expression cassettes.

4. The method of claim 2, wherein said at least one expression cassette expresses E1 and E2 glycoproteins.

5. The method of claim 1, further comprising the step of overlaying said infected cells with a layer of agarose prior to step (c).

* * * * *